(12) United States Patent
Martin et al.

(10) Patent No.: US 9,943,323 B2
(45) Date of Patent: *Apr. 17, 2018

(54) RETRIEVAL SYSTEMS AND METHODS FOR USE THEREOF

(71) Applicant: Covidien LP, Mansfield, MA (US)

(72) Inventors: Brian Martin, Felton, CA (US); Martin Dieck, Campbell, CA (US)

(73) Assignee: COVIDIEN IP, Mansfield, MA (US)

( * ) Notice: Subject to any disclaimer, the term of this patent is extended or adjusted under 35 U.S.C. 154(b) by 207 days.

This patent is subject to a terminal disclaimer.

(21) Appl. No.: 15/174,016

(22) Filed: Jun. 6, 2016

(65) Prior Publication Data

US 2016/0354098 A1 Dec. 8, 2016

Related U.S. Application Data

(63) Continuation of application No. 14/446,755, filed on Jul. 30, 2014, now Pat. No. 9,358,094, which is a continuation of application No. 13/959,433, filed on Aug. 5, 2013, now Pat. No. 8,795,305, which is a continuation of application No. PCT/US2012/039216, filed on May 23, 2012.

(Continued)

(51) Int. Cl.

| A61F 2/06 | (2013.01) |
| A61B 17/221 | (2006.01) |
| A61B 17/3207 | (2006.01) |
| A61F 2/01 | (2006.01) |
| A61F 2/95 | (2013.01) |
| A61F 2/962 | (2013.01) |
| A61B 17/22 | (2006.01) |
| A61B 17/34 | (2006.01) |

(52) U.S. Cl.
CPC ...... *A61B 17/221* (2013.01); *A61B 17/22031* (2013.01); *A61B 17/3207* (2013.01); *A61B 17/320758* (2013.01); *A61F 2/01* (2013.01); *A61F 2/06* (2013.01); *A61F 2/95* (2013.01); *A61F 2/962* (2013.01); *A61B 2017/22034* (2013.01); *A61B 2017/3435* (2013.01); *A61B 2560/04* (2013.01); *A61F 2002/011* (2013.01); *A61F 2230/0006* (2013.01); *A61F 2230/0093* (2013.01)

(58) Field of Classification Search
CPC .......... A61B 17/221; A61B 2017/2212; A61B 2017/2215; A61B 2017/3435; A61F 2230/0006; A61F 2/013
USPC ........................................ 606/127, 159, 200
See application file for complete search history.

(56) References Cited

U.S. PATENT DOCUMENTS

| 2,918,919 A | 12/1959 | Wallace |
| 2,943,626 A | 7/1960 | Dormia |

(Continued)

FOREIGN PATENT DOCUMENTS

| CN | 1640505 A | 7/2005 |
| CN | 102036611 A | 4/2011 |

(Continued)

*Primary Examiner* — Katherine M Shi
(74) *Attorney, Agent, or Firm* — Fortem IP LLP; Mary Fox

(57) ABSTRACT

The devices and methods described herein relate to improved structures for removing obstructions from body lumens. Such devices have applicability in through-out the body, including clearing of blockages within the vasculature, by addressing the frictional resistance on the obstruction prior to attempting to translate and/or mobilize the obstruction within the body lumen.

64 Claims, 27 Drawing Sheets

Related U.S. Application Data

(60) Provisional application No. 61/489,254, filed on May 24, 2011, provisional application No. 61/489,183, filed on May 23, 2011.

(56) References Cited

U.S. PATENT DOCUMENTS

| | | |
|---|---|---|
| 3,996,938 A | 12/1976 | Clark, III |
| 4,347,846 A | 9/1982 | Dormia |
| 4,611,594 A | 9/1986 | Grayhack et al. |
| 4,650,466 A | 3/1987 | Luther |
| 4,657,020 A | 4/1987 | Lifton |
| 4,699,147 A | 10/1987 | Chilson et al. |
| 4,790,812 A | 12/1988 | Hawkins, Jr. et al. |
| 4,807,626 A | 2/1989 | McGirr |
| 4,832,055 A | 5/1989 | Palestrant |
| 4,873,978 A | 10/1989 | Ginsburg |
| 4,969,891 A | 11/1990 | Gewertz |
| 4,998,539 A | 3/1991 | Delsanti |
| 5,034,001 A | 7/1991 | Garrison et al. |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A | 3/1993 | Phan et al. |
| 5,300,086 A | 4/1994 | Gory et al. |
| 5,329,942 A | 7/1994 | Gunther et al. |
| 5,443,478 A | 8/1995 | Purdy |
| 5,449,372 A | 9/1995 | Schmaltz et al. |
| 5,458,375 A | 10/1995 | Anspach, Jr. et al. |
| 5,490,859 A | 2/1996 | Mische et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,941,869 A | 8/1999 | Patterson et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 5,984,957 A | 11/1999 | Laptewicz, Jr. et al. |
| 6,001,118 A | 12/1999 | Daniel et al. |
| 6,033,394 A | 3/2000 | Vidlund et al. |
| 6,042,598 A | 3/2000 | Tsugita et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,146,403 A | 11/2000 | St. Germain |
| 6,159,220 A | 12/2000 | Gobron et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,176,873 B1 | 1/2001 | Ouchi |
| 6,190,394 B1 | 2/2001 | Lind et al. |
| 6,217,609 B1 | 4/2001 | Haverkost |
| 6,221,006 B1 | 4/2001 | Dubrul et al. |
| 6,245,088 B1 | 6/2001 | Lowery |
| 6,245,089 B1 | 6/2001 | Daniel et al. |
| 6,248,113 B1 | 6/2001 | Fina |
| 6,264,664 B1 | 7/2001 | Avellanet |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,391,044 B1 | 5/2002 | Yadav et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,485,497 B2 | 11/2002 | Wensel et al. |
| 6,494,884 B2 | 12/2002 | Gifford, III et al. |
| 6,506,204 B2 | 1/2003 | Mazzocchi |
| 6,514,273 B1 | 2/2003 | Voss et al. |
| 6,530,935 B2 | 3/2003 | Wensel et al. |
| 6,540,657 B2 | 4/2003 | Cross, III et al. |
| 6,540,768 B1 | 4/2003 | Diaz et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,855,155 B2 | 2/2005 | Denardo et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford, III et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,041,126 B2 | 5/2006 | Shin et al. |
| 7,048,014 B2 | 5/2006 | Hyodoh et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,240,516 B2 | 7/2007 | Pryor |
| 7,399,308 B2 | 7/2008 | Borillo et al. |
| 7,534,252 B2 | 5/2009 | Sepetka et al. |

(56) References Cited

U.S. PATENT DOCUMENTS

| | | |
|---|---|---|
| 7,578,830 B2 | 8/2009 | Kusleika et al. |
| 7,621,870 B2 | 11/2009 | Berrada et al. |
| 7,837,702 B2 | 11/2010 | Bates |
| 8,070,791 B2 | 12/2011 | Ferrera et al. |
| 8,088,140 B2 | 1/2012 | Ferrera et al. |
| 8,105,333 B2 | 1/2012 | Sepetka et al. |
| 8,197,493 B2 | 6/2012 | Ferrera et al. |
| 2001/0041909 A1 | 11/2001 | Tsugita et al. |
| 2001/0044632 A1 | 11/2001 | Daniel et al. |
| 2001/0044634 A1 | 11/2001 | Don Michael et al. |
| 2001/0051810 A1 | 12/2001 | Dubrul et al. |
| 2002/0002396 A1 | 1/2002 | Fulkerson |
| 2002/0004667 A1 | 1/2002 | Adams et al. |
| 2002/0026211 A1 | 2/2002 | Khosravi et al. |
| 2002/0058904 A1 | 5/2002 | Boock et al. |
| 2002/0062135 A1 | 5/2002 | Mazzocchi et al. |
| 2002/0072764 A1 | 6/2002 | Sepetka et al. |
| 2002/0082558 A1 | 6/2002 | Samson et al. |
| 2002/0123765 A1 | 9/2002 | Sepetka et al. |
| 2002/0138094 A1 | 9/2002 | Borillo et al. |
| 2002/0151928 A1 | 10/2002 | Leslie et al. |
| 2002/0169474 A1 | 11/2002 | Kusleika et al. |
| 2002/0188314 A1 | 12/2002 | Anderson et al. |
| 2002/0193825 A1 | 12/2002 | McGuckin et al. |
| 2003/0004542 A1 | 1/2003 | Wensel et al. |
| 2003/0023265 A1 | 1/2003 | Forber |
| 2003/0040771 A1 | 2/2003 | Hyodoh et al. |
| 2003/0050663 A1 | 3/2003 | Khachin et al. |
| 2003/0060782 A1 | 3/2003 | Bose et al. |
| 2003/0093087 A1 | 5/2003 | Jones et al. |
| 2003/0144687 A1 | 7/2003 | Brady et al. |
| 2003/0153935 A1 | 8/2003 | Mialhe |
| 2003/0176884 A1 | 9/2003 | Berrada et al. |
| 2003/0195556 A1 | 10/2003 | Stack et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0133232 A1 | 7/2004 | Rosenbluth et al. |
| 2004/0138692 A1 | 7/2004 | Phung et al. |
| 2004/0153025 A1 | 8/2004 | Seifert et al. |
| 2004/0153118 A1 | 8/2004 | Clubb et al. |
| 2004/0172056 A1 | 9/2004 | Guterman et al. |
| 2004/0199201 A1 | 10/2004 | Kellett et al. |
| 2004/0199243 A1 | 10/2004 | Yodfat |
| 2004/0210116 A1 | 10/2004 | Nakao |
| 2004/0267301 A1 | 12/2004 | Boylan et al. |
| 2005/0004594 A1 | 1/2005 | Nool et al. |
| 2005/0033348 A1 | 2/2005 | Sepetka et al. |
| 2005/0038447 A1 | 2/2005 | Huffmaster |
| 2005/0043680 A1 | 2/2005 | Segal et al. |
| 2005/0043756 A1 | 2/2005 | Lavelle et al. |
| 2005/0049619 A1 | 3/2005 | Sepetka et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0080356 A1 | 4/2005 | Dapolito et al. |
| 2005/0085826 A1 | 4/2005 | Nair et al. |
| 2005/0085847 A1 | 4/2005 | Galdonik et al. |
| 2005/0085849 A1 | 4/2005 | Sepetka et al. |
| 2005/0090857 A1 | 4/2005 | Kusleika et al. |
| 2005/0090858 A1 | 4/2005 | Pavlovic |
| 2005/0125024 A1 | 6/2005 | Sepetka et al. |
| 2005/0131450 A1 | 6/2005 | Nicholson et al. |
| 2005/0171566 A1 | 8/2005 | Kanamaru |
| 2005/0203571 A1 | 9/2005 | Mazzocchi et al. |
| 2005/0209609 A1 | 9/2005 | Wallace |
| 2005/0216030 A1 | 9/2005 | Sepetka et al. |
| 2005/0216050 A1 | 9/2005 | Sepetka et al. |
| 2005/0234501 A1 | 10/2005 | Barone |
| 2005/0234505 A1 | 10/2005 | Diaz et al. |
| 2005/0277978 A1 | 12/2005 | Greenhalgh |
| 2005/0283166 A1 | 12/2005 | Greenhalgh |
| 2005/0283186 A1 | 12/2005 | Berrada et al. |
| 2006/0004404 A1 | 1/2006 | Khachin et al. |
| 2006/0009784 A1 | 1/2006 | Behl et al. |
| 2006/0030925 A1 | 2/2006 | Pryor |
| 2006/0047286 A1 | 3/2006 | West |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0095070 A1 | 5/2006 | Gilson et al. |
| 2006/0129166 A1 | 6/2006 | Lavelle |
| 2006/0129180 A1 | 6/2006 | Tsugita et al. |
| 2006/0155305 A1 | 7/2006 | Freudenthal et al. |
| 2006/0190070 A1 | 8/2006 | Dieck et al. |
| 2006/0195137 A1 | 8/2006 | Sepetka et al. |
| 2006/0229638 A1 | 10/2006 | Abrams et al. |
| 2006/0253145 A1 | 11/2006 | Lucas |
| 2006/0271153 A1 | 11/2006 | Garcia et al. |
| 2006/0276805 A1 | 12/2006 | Yu |
| 2006/0282111 A1 | 12/2006 | Morsi |
| 2006/0287668 A1 | 12/2006 | Fawzi et al. |
| 2007/0112374 A1 | 5/2007 | Paul et al. |
| 2007/0118165 A1 | 5/2007 | DeMello et al. |
| 2007/0149996 A1 | 6/2007 | Coughlin |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0198051 A1 | 8/2007 | Clubb et al. |
| 2007/0225749 A1 | 9/2007 | Martin et al. |
| 2007/0233236 A1 | 10/2007 | Pryor |
| 2007/0265656 A1 | 11/2007 | Amplatz et al. |
| 2008/0109031 A1 | 5/2008 | Sepetka et al. |
| 2008/0183198 A1 | 7/2008 | Sepetka et al. |
| 2008/0188885 A1 | 8/2008 | Sepetka et al. |
| 2008/0262528 A1 | 10/2008 | Martin |
| 2008/0262532 A1 | 10/2008 | Martin |
| 2009/0069828 A1 | 3/2009 | Martin et al. |
| 2009/0105722 A1 | 4/2009 | Fulkerson et al. |
| 2009/0105737 A1 | 4/2009 | Fulkerson et al. |
| 2009/0125053 A1 | 5/2009 | Ferrera et al. |
| 2009/0192518 A1 | 7/2009 | Golden et al. |
| 2009/0287291 A1 | 11/2009 | Becking et al. |
| 2009/0299393 A1 | 12/2009 | Martin et al. |
| 2010/0076452 A1 | 3/2010 | Sepetka et al. |
| 2010/0100106 A1 | 4/2010 | Ferrera |
| 2010/0174309 A1 | 7/2010 | Fulkerson et al. |
| 2010/0185210 A1 | 7/2010 | Hauser et al. |
| 2010/0217187 A1 | 8/2010 | Fulkerson et al. |
| 2010/0256600 A1 | 10/2010 | Ferrera |
| 2010/0318097 A1 | 12/2010 | Ferrera et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0288572 A1 | 11/2011 | Martin |
| 2011/0319917 A1 | 12/2011 | Ferrera et al. |
| 2012/0143230 A1 | 6/2012 | Sepetka et al. |
| 2012/0197285 A1 | 8/2012 | Martin et al. |
| 2016/0354098 A1 | 12/2016 | Martin et al. |

FOREIGN PATENT DOCUMENTS

| | | |
|---|---|---|
| DE | 3501707 A1 | 7/1986 |
| EP | 200668 A2 | 11/1986 |
| EP | 1312314 A1 | 5/2003 |
| JP | 2002537943 A | 11/2002 |
| JP | 2007-522881 A | 8/2007 |
| JP | 2007252951 A | 10/2007 |
| JP | 2008539958 A | 11/2008 |
| JP | 2011508635 | 3/2011 |
| WO | WO-94/09845 A1 | 5/1994 |
| WO | WO-95/09586 A1 | 4/1995 |
| WO | WO-9601591 A1 | 1/1996 |
| WO | WO-96/17634 A2 | 6/1996 |
| WO | WO-96/19941 A1 | 7/1996 |
| WO | WO-97/27808 A1 | 8/1997 |
| WO | WO-97/27893 A1 | 8/1997 |
| WO | WO-98/03120 A1 | 1/1998 |
| WO | WO-00/53120 A1 | 9/2000 |

(56) References Cited

FOREIGN PATENT DOCUMENTS

| | | |
|---|---|---|
| WO | WO-0072909 A1 | 12/2000 |
| WO | WO-01/32254 A1 | 5/2001 |
| WO | WO-01/54622 A1 | 8/2001 |
| WO | WO-01/67967 A1 | 9/2001 |
| WO | WO-02/02162 | 1/2002 |
| WO | WO-02/28291 A2 | 4/2002 |
| WO | WO-03/000334 A1 | 1/2003 |
| WO | WO-03/061730 A2 | 7/2003 |
| WO | WO-03/089039 A1 | 10/2003 |
| WO | WO-2006/031410 A2 | 3/2006 |
| WO | WO-2006/122076 A1 | 11/2006 |
| WO | WO-2007092820 A2 | 8/2007 |
| WO | WO-2008/036156 A1 | 3/2008 |
| WO | WO-2008036156 | 3/2008 |
| WO | WO-2008/131116 A1 | 10/2008 |
| WO | WO-2009/034456 A2 | 3/2009 |
| WO | WO-2009/086482 A1 | 7/2009 |
| WO | WO-2011/091383 A1 | 7/2011 |
| WO | WO-2011091383 | 7/2011 |
| WO | WO-2012009675 A2 | 1/2012 |
| WO | WO-2012/162437 A1 | 11/2012 |
| WO | WO-2013/106146 A1 | 7/2013 |

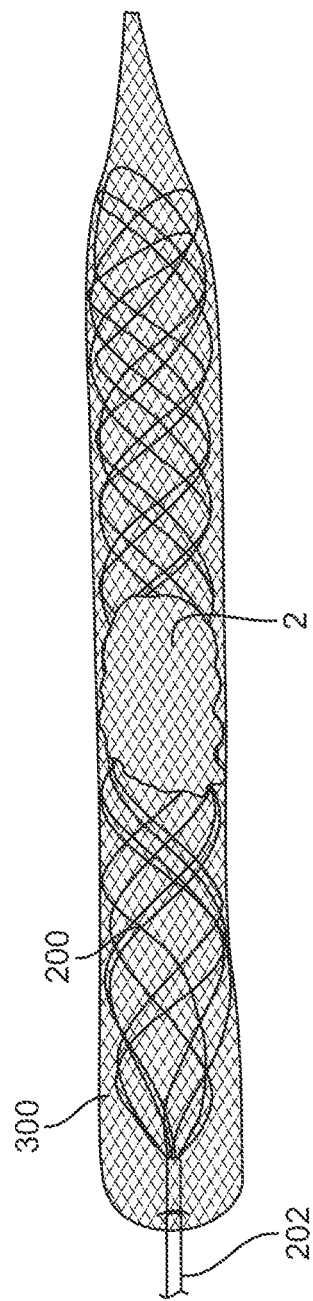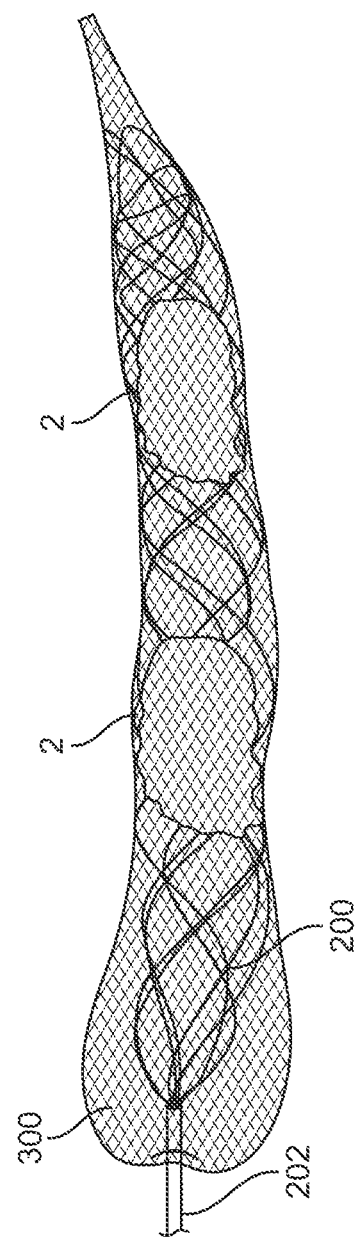

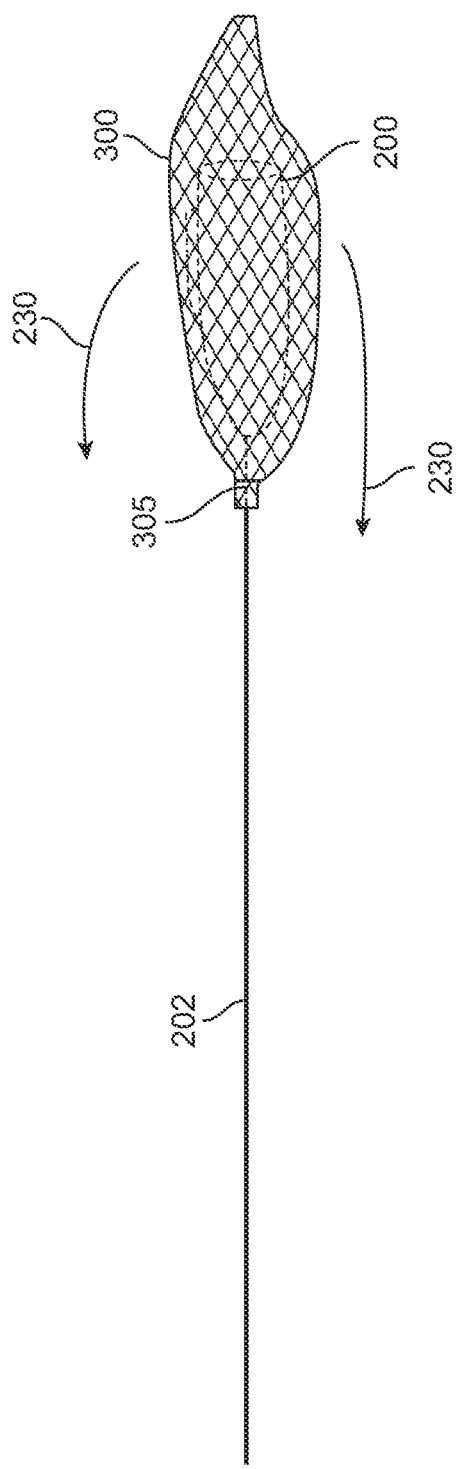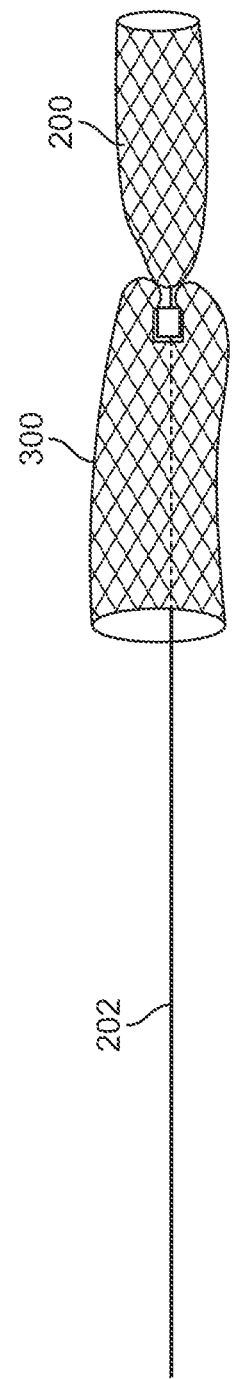
FIG. 5K
FIG. 5L

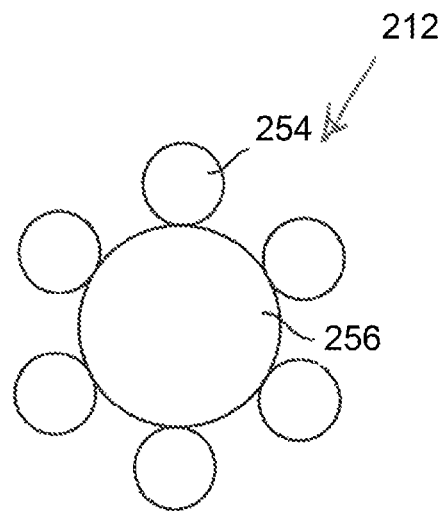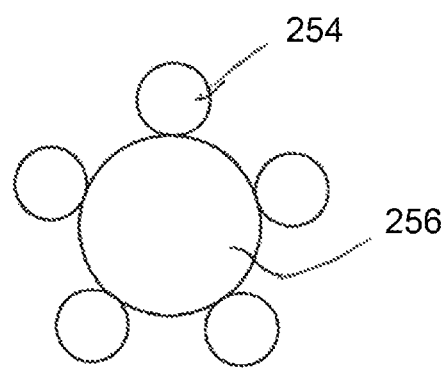
FIG. 9A      FIG. 9B
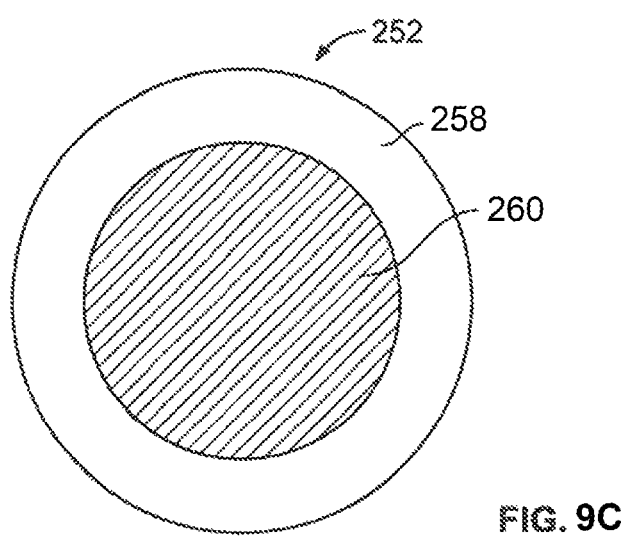
FIG. 9C

RETRIEVAL SYSTEMS AND METHODS FOR USE THEREOF

CROSS-REFERENCE TO RELATED APPLICATIONS

This application is a continuation of U.S. application Ser. No. 14/446,755 filed Jul. 30, 2014, now U.S. Pat. No. 9,358,094, which is a continuation of U.S. application Ser. No. 13/959,433 filed Aug. 5, 2013, now U.S. Pat. No. 8,795,305, which is a continuation of PCT Application No. PCT/US2012/039216 filed May 23, 2012, which is a non-provisional of U.S. Provisional Application No. 61/489,183 filed May 23, 2011, and 61/489,254 filed May 24, 2011. The entirety of each of the above-mentioned prior applications is hereby incorporated by reference.

FIELD OF THE INVENTION

The devices described herein are intended to retrieve obstructions from the body. Such devices have applicability throughout the body, including clearing of blockages within body lumens and providing passive protection of such, such as the vasculature, by providing a capturing portion that can translate and/or mobilize the obstruction within the body lumen.

BACKGROUND OF THE INVENTION

A large number of medical procedures require the use of medical device(s) to remove an obstruction from a body lumen, vessel, or other organ. An inherent risk in such procedures is that mobilizing or otherwise disturbing the obstruction can potentially create further harm if the obstruction or a fragment thereof dislodges from the retrieval device. If a particle or the obstruction breaks free from the device and flows downstream, it is highly likely that the particle or obstruction will become trapped in smaller and more tortuous anatomy. In many cases, the physician will no longer be able to use the same retrieval device to again remove the obstruction because the size of the device may prevent advancing the device to the site of the new obstruction.

Even in successful procedures, a physician must proceed with caution to prevent the walls of the vessel or body lumen from imparting undesired forces to shear or dislodge the obstruction as it is translated through the body during removal. These forces have the potential of breaking portions or fragments of the obstruction away. In some cases, the obstruction can simply break free from the retrieval device and can lodge in a new area causing more concern than the original blockage.

Procedures for restoring flow within the cerebral vasculature as a result of ischemic stroke are one example of where these issues present a concern. The brain relies on its arteries and veins to supply oxygenated blood from the heart and lungs and to remove carbon dioxide and cellular waste from brain tissue. Blockages that interfere with this supply eventually cause the brain tissue to stop functioning. If the disruption in supply occurs for a sufficient amount of time, the continued lack of nutrients and oxygen causes irreversible cell death (infarction). Accordingly, immediate medical treatment of an ischemic stroke is critical for the recovery of a patient. To access the cerebral vasculature a physician typically advances a catheter from a remote part of the body (typically a leg) through the vasculature and into the cerebral region of the vasculature. Once within the cerebral region, the physician deploys a device for retrieval of the obstruction causing the blockage. Concerns about dislodged obstructions or the migration of dislodged fragments increases the duration of the procedure at time when restoration of blood flow is paramount. Furthermore, a physician might be unaware of one or more fragments that dislodge from the initial obstruction and cause blockage of smaller more distal vessels.

Many physicians currently use stents to perform thrombectomy (i.e. clot removal) to resolve ischemic stroke. Typically, the physician deploys the stent into the clot, in an attempt to push the clot to the side of the vessel and re-establish blood to flow. Tissue plasminogen activator ("Tpa") is often injected into the bloodstream through an intravenous line. The TPA must travel in the blood stream until it reaches the clot that is causing the blockage. Once the Tpa contacts the clot, it begins to break up the clot with the hope of restoring blood flow to the affected areas. Tpa is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot from the vessel, in a proximal direction, into a guide catheter located within vessels in the patients neck (typically the carotid artery). While this procedure has been shown to be effective in the clinic and easy for the physician to perform, there remain some distinct disadvantages using this approach.

The stent may not sufficiently hold onto the clot as it drags the clot to the catheter. In such a case, the clot might not move from the vessel. Another risk is that use of the stent might mobilize the clot might from the original blockage site, but the clot might not adhere to the stent during translation toward the catheter. This is a particular risk when translating through bifurcations and tortuous anatomy. Furthermore, blood flow can migrate the clot (or fragments of the clot) into a branching vessel at a bifurcation. If the clot is successfully brought to the guide catheter in the carotid artery, yet another risk is that the clot may be "stripped" or "sheared" from the stent as the stent enters the guide catheter. Regardless, simply dragging an expanded stent (either fully or partially expanded) can result in undesired trauma to the vessel. In most cases, the stent is oversized compared to the vessel. Dragging a fixed metallic (or other) structure can pull the arteries and/or strip the cellular lining from the vessel, causing further trauma such as a hemorrhagic stroke (leakage of blood from a cerebral vessel). Also, the stent can become lodged on plaque on the vessel walls resulting in further vascular damage.

In view of the above, there remains a need for improved devices and methods that can remove occlusions from body lumens and/or vessels. While the discussion focuses on applications in the cerebral vasculature, the improved devices and methods described below have applications outside of the area of ischemic stroke.

SUMMARY OF THE INVENTION

The examples discussed herein show the inventive device in a form that is suitable to retrieve obstructions or clots within the vasculature. The term obstructions may include blood clot, plaque, cholesterol, thrombus, naturally occurring foreign bodies (i.e., a part of the body that is lodged within the lumen), a non-naturally occurring foreign body (i.e., a portion of a medical device or other non-naturally occurring substance lodged within the lumen.) However, the devices are not limited to such applications and can apply to any number of medical applications where elimination or reduction of the number of connection points is desired.

The devices discussed herein include interventional medical devices for retrieving and securing an obstruction within a vessel lumen. In one variation, the device includes a shaft having a flexibility to navigate through tortuous anatomy, the shaft having a distal portion and a proximal portion and a lumen extending therethrough; and an eversible cover having a fixed section affixed near an end of the distal portion of the shaft, a free section extending in a proximal direction from the fixed section and a cover wall extending from the fixed section to the free section, where the eversible cover is expandable against a vessel wall, the eversible cover being axially compliant such that when the interventional vascular device retrieval device is positioned through the shaft lumen and moved in a proximal direction, the friction of the eversible cover against the vessel wall causes the eversible cover to evert over the interventional vascular device allowing for the free section of the cover to be distal to the interventional vascular device.

In another variation, the present disclosure includes a method of securing an obstruction within a vessel. For example, the method can include advancing a shaft having a retrieval device affixed thereto to the obstruction; advancing a protective device over the shaft, the protective device comprising a sheath having an eversible cover, where a fixed end of the eversible cover is affixed to a distal portion of the sheath and a free end of the eversible cover is located proximal to the fixed end; positioning the fixed end of the eversible cover adjacent to the retrieval device and expanding at least a portion of the eversible cover against a portion of a wall of the vessel; proximally translating the shaft and retrieval device with at least a portion of the obstruction affixed thereto such that resistance of the eversible cover against the vessel resists movement of the eversible cover causing the free section of the eversible cover to evert over the proximally translated retrieval device.

Another variation of the method include securing an obstruction within a vessel of a patient, by providing an interventional vascular device having a wire attached thereto, where the interventional vascular device is configured to remove the obstruction from the vessel; coupling a shaft to the wire of the interventional vascular device, the shaft having a distal portion and a proximal portion and a lumen extending therethrough and having a flexibility to navigate through tortuous anatomy, an eversible cover having a fixed section affixed near an end of the distal portion of the shaft, a free section extending in a proximal direction from the fixed section and a cover wall extending from the fixed section to the free section, where the eversible cover is expandable against a vessel wall, the eversible cover being axially compliant such that when the interventional vascular device retrieval device is positioned through the shaft lumen and moved in a proximal direction against the eversible cover, the friction of the eversible cover against the vessel wall causes the eversible cover to evert over the interventional vascular device allowing for the free section of the cover to be distal to the interventional vascular device; positioning the shaft and eversible cover over the wire of the interventional vascular device prior to insertion into the patient; and advancing the interventional vascular device, shaft and eversible cover into the vessel to the obstruction. The device can also be configured so that the fixed section of the eversible cover comprises a pre-set shape to reduce a force required to evert the evertable cover.

The retrieval devices can comprise any number of capturing or retrieval device such as a filter, an artherectomy device, a rotational cutter, an aspiration device, stent based retrievers and retrieval baskets.

The methods described herein can include methods of securing an obstruction within a vessel. In one example, the method can comprise: positioning a catheter within a vessel; advancing a shaft having a retrieval device affixed thereto out of the catheter; advancing an eversible cover out of the catheter such that a fixed end of the eversible cover is affixed adjacent to a proximal end of the retrieval device and a free end of the eversible cover is moveable relative to the shaft and retrieval device; expanding a at least a portion of the eversible cover against a portion of a wall of the vessel; manipulating the retrieval device to become at least partially enmeshed with the obstruction; and proximally translating the shaft and retrieval device with at least a portion of the obstruction affixed thereto such that resistance of the eversible cover against the vessel resists movement of the eversible cover causing the free section of the eversible cover to evert over the proximally translated retrieval device.

In another variation, the methods can include further withdrawing the shaft from the vessel such that during withdrawal the eversible cover forms a protective barrier over the obstruction to lessen shearing forces caused by the vessel and reduce dislodging portions of the obstruction from the retrieval device.

Another variation of a method includes a method of preparing a retrieval device comprising: providing a retrieval device having been previously removed from a body of a patient where the retrieval device includes a protective cover where a fixed end of the protective cover is affixed adjacent to a proximal end of the retrieval device and where a free end is located distally to the fixed end covering the retrieval device and is moveable relative to the second end; reversing the protective cover by moving the free end proximally of the fixed while the fixed end remains affixed adjacent to the proximal end of the retrieval device; inserting the retrieval device and cover into a catheter where the free end of the cover is proximal to the fixed end of the cover and retrieval device such that upon deployment from the catheter, the free end of the cover deploys proximally to the fixed end of the cover.

In another example, the devices described herein can include medical device retrieval systems for securing an obstruction within a vessel lumen and for use with a catheter configured to be navigated through the vasculature. In one variation, the device comprises an elongated stent comprising a plurality of struts, the stent being collapsible for positioning in the catheter during delivery and having an expanded profile such that when expanded the struts are configured to engage the obstruction; a shaft fixedly attached to the elongated stent and having a flexibility to navigate through tortuous anatomy; a fluid permeable cover having a distal end coupled to a proximal end of the elongated stent a cover wall defining a cavity and extending along the shaft, and a proximal end being moveable relative to the shaft, where the fluid permeable cover is collapsible for positioning in the catheter during delivery and is expandable upon deployment from the catheter such that at least a portion of the fluid permeable cover is expandable; where the fluid permeable cover is axially pliable such that when the device is deployed in the vessel the frictional forces between the vessel and the fluid permeable cover permit proximal movement of the shaft and elongated stent to cause inversion of the fluid permeable cover wall such that the fluid permeable cover wall everts over the elongated stent.

Another variation of a device includes an interventional medical device for use with a catheter configured for delivery through vasculature for securing an obstruction within a vessel lumen. For example, the device can comprise a shaft having a flexibility to navigate through tortuous anatomy, the shaft having a distal portion and a proximal portion; a capturing device comprising a sidewall, the capturing device fixedly located at a distal portion of the shaft and having a reduced profile for positioning in the catheter and an expanded profile, such that upon deployment from the catheter, the capturing device expands to force a portion of the sidewall into the obstruction to at least partially attach to the obstruction; a cover having a distal end coupled adjacent to a proximal end of the capturing structure, a proximal end and a cover wall extending therebetween, where the proximal end of the cover is slidable relative to the distal end, where the cover is expandable such that when located in the catheter the cover is in a reduced delivery state and upon advancement from the catheter the cover expands with the proximal end located proximally of the distal end, where the cover wall is compliant such that when deployed from the catheter and the shaft is pulled in a proximal direction frictional forces between the vessel and the cover wall or proximal end cause the cover to invert as the cover wall inverts over the capturing device to surround the capturing device.

Another variation of the device includes an interventional medical device for securing a retrieval device having one or more obstructions located therein for removal from a body. In one such example the medical device includes a sheath having a flexibility to navigate through tortuous anatomy, the sheath a distal portion and a proximal portion and a lumen extending therethrough; an eversible cover having a fixed section affixed to the distal portion of the sheath, a free section extending in a proximal direction from the fixed section and a cover wall extending from the fixed section to the free section, where the eversible cover is expandable, the eversible cover being axially compliant such that when the retrieval device is positioned through the sheath lumen moved in a proximal direction against the eversible cover, the eversible cover everts over the retrieval device allowing for the free section of the cover to be distal to the retrieval device.

Another variation of the method includes advancing a shaft having a retrieval device affixed thereto to the obstruction; advancing a protective device over the shaft, the protective device comprising a sheath having an eversible cover, where a fixed end of the eversible cover is affixed to a distal portion of the sheath and a free end of the eversible cover is located proximal to the fixed end; positioning the fixed end of the eversible cover adjacent to the retrieval device and expanding at least a portion of the eversible cover against a portion of a wall of the vessel; proximally translating the shaft and retrieval device with at least a portion of the obstruction affixed thereto such that resistance of the eversible cover against the vessel resists movement of the eversible cover causing the free section of the eversible cover to evert over the proximally translated retrieval device.

The capturing portions described herein can include a stent retrieval device for expanding against one or more occlusive bodies in a vasculature. In one example, the stent retrieval device includes an elongate shaft having a flexibility to navigate through tortuous anatomy, the elongate shaft having a distal portion and a proximal portion; a plurality of filaments that diverge from the distal portion of the elongate shaft to form an expandable elongated stent body having a open distal end and a fluid permeable closed proximal end and a cavity therebetween, where divergence of the filaments at the distal portion of the elongate shaft forms the fluid permeable closed proximal end; where the plurality of filaments extending along the shaft are free of any connection joints in the distal portion to permit increased flexibility of the distal portion as it navigates though tortuous anatomy; and one or more connection joints proximal to the distal portion where the connection joints secure the plurality of filaments to the shaft.

The stent retrieval can also include at least one of the plurality of filaments that comprise at least two wires twisted together, the elongated stent body further comprising at least one intersection of filaments, where the wires of each filament are interwoven to provide increased outward radial strength of the elongated stent body and such that the wires slide relative to each other as the elongated stent body expands or compresses in diameter to reduce a force required to linearize the elongated stent body.

The stent retrieval device can have an exterior surface of the elongated stent body that comprises an irregular surface formed by intersection of filaments.

The stent retrieval device can also have intersection of filaments comprising a barb or knuckle and where a plurality of barbs or knuckles is radially spaced about the elongated stent body. The stent retrieval device can also have an intersection of filaments that comprises a barb or knuckle and where a plurality of barbs or knuckles is aligned with an axis of the elongated stent body.

In one variation of the devices described herein, the device comprises a main bundle or group of wires that diverge to form a device having various shapes but few or no connections points or joints (where fabrication of such a construction is referred to as "jointless"). Clearly, the inventive devices described herein are not limited to such a jointless construction. Additional variation includes one or more leading wires that are attached to a capturing portion as described below.

Devices of the present invention can incorporate any number of wires of different characteristics including, but not limited to, materials, shapes, sizes and/or diameters. Clearly, the number of permutations of device configurations is significant. Providing devices with such a composite construction allows for the manipulation of the device's properties to suite the intended application.

As noted herein, the joint-less construction improves the flexibility and strength of the device by eliminating joints, connection points, or other attachment points. In addition, the joint-less construction improves the ability of the device to be delivered through a small microcatheter. As a result, the device and microcatheter are able to access remote regions of the vasculature.

The devices may be fabricated to be self-expanding upon deployment from a catheter. Alternatively, the devices can be constructed from shape-memory alloys such that they automatically deploy upon reaching a pre-determined transition temperature.

It should be noted that in some variations of the invention, all or some of the device can be designed to increase their ability to adhere to the obstruction. For example, the wires may be coupled to an energy source (e.g., RF, ultrasonic, or thermal energy) to "weld" to the obstruction. Application of energy to the device can allow the surrounding portion to deform into the obstruction and "embed" within the obstruction. Alternatively, the device can impart a positive charge to the obstruction to partially liquefy the obstruction sufficiently to allow for easier removal. In another variation, a negative charge could be applied to further build thrombus and nest the device for better pulling force. The wires can be made stickier by use of a hydrophilic substance(s), or by chemicals that would generate a chemical bond to the surface of the obstruction. Alternatively, the filaments may reduce the temperature of the obstruction to congeal or adhere to the obstruction.

Additional devices and methods for treating ischemic stroke are discussed in commonly assigned U.S. patent application Ser. No. 11/671,450 filed Feb. 5, 2007; Ser. No. 11/684,521 filed Mar. 9, 2007; Ser. No. 11/684,535 filed Mar. 9, 2007; Ser. No. 11/684,541 filed Mar. 9, 2007; Ser. No. 11/684,546 filed Mar. 9, 2007; Ser. No. 11/684,982 filed Mar. 12, 2007, Ser. No. 11/736,526 filed Apr. 17, 2007, Ser. No. 11/736,537 filed Apr. 17, 2007, Ser. No. 11/825,975 filed Sep. 10, 2007; Ser. No. 12/344,378 filed Dec. 26, 2008, Ser. No. 13/012,727 filed Jan. 24, 2011, and Ser. No. 13/226,222 filed Sep. 6, 2011; the entirety of each of which is incorporated by reference. The principles of the invention as discussed herein may be applied to the above referenced cases to produce devices useful in treating ischemic stroke. In other words, the wire-shaped construction of devices according to present invention may assume the shapes disclosed in the above-referenced cases when such a combination is not inconsistent with the features described herein.

BRIEF DESCRIPTION OF THE DRAWINGS

Each of the following figures diagrammatically illustrates aspects of the invention. Variation of the invention from the aspects shown in the figures is contemplated.

FIGS. 4J and 4K illustrate examples of an obstruction or other material captured within a retrieval device with a cover further protecting the loaded retrieval device.

FIGS. 5K and 5L show a variation of a cover and retrieval device where the cover is first mounted in a distal direction and then inverted in a proximal direction.

FIGS. 9A to 9C illustrate wires of different constructions within a delivery wire or shaft.

DETAILED DESCRIPTION

It is understood that the examples below discuss uses in the cerebral vasculature (namely the arteries). However, unless specifically noted, variations of the device and method are not limited to use in the cerebral vasculature. Instead, the invention may have applicability in various parts of the body. Moreover, the invention may be used in various procedures where the benefits of the method and/or device are desired.

Figure 1:
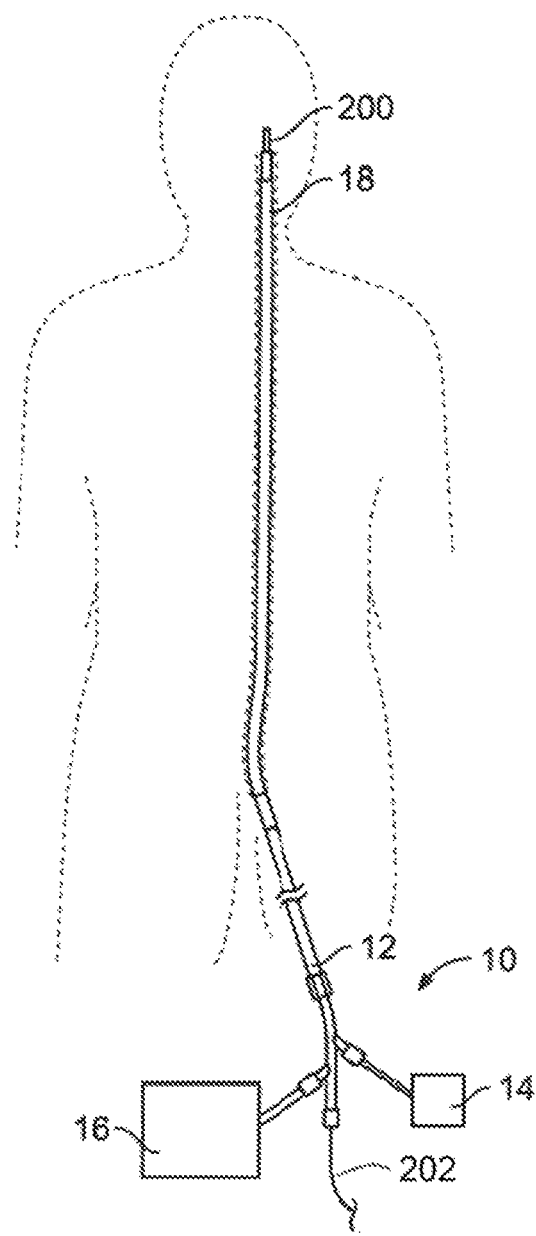
FIG. 1 illustrates an example of a device according to the present invention when used in a system for removing obstructions from body lumens.

FIG. 1 illustrates a system 10 for removing obstructions from body lumens as described herein.

In the illustrated example, this variation of the system 10 is suited for removal of an obstruction in the cerebral vasculature. As stated herein, the present devices and methods are useful in other regions of the body including the vasculature and other body lumens or organs. For exemplary purposes, the discussion shall focus on uses of these devices and method in the vasculature.

It is noted that any number of catheters or microcatheters maybe used to locate the catheter/microcatheter 12 carrying the obstruction removal device 200 at the desired target site. Such techniques are well understood standard interventional catheterization techniques. Furthermore, the catheter 12 may be coupled to auxiliary or support components 14, 16 (e.g., energy controllers, power supplies, actuators for movement of the device(s), vacuum sources, inflation sources, sources for therapeutic substances, pressure monitoring, flow monitoring, various bio-chemical sensors, bio-chemical substance, etc.) Again, such components are within the scope of the system 10 described herein.

In addition, devices of the present invention may be packaged in kits including the components discussed above along with guiding catheters, various devices that assist in the stabilization or removal of the obstruction (e.g., proximal-assist devices that holds the proximal end of the obstruction in place preventing it from straying during removal or assisting in the removal of the obstruction), balloon-tipped guide catheters, dilators, etc.

Figure 2A:
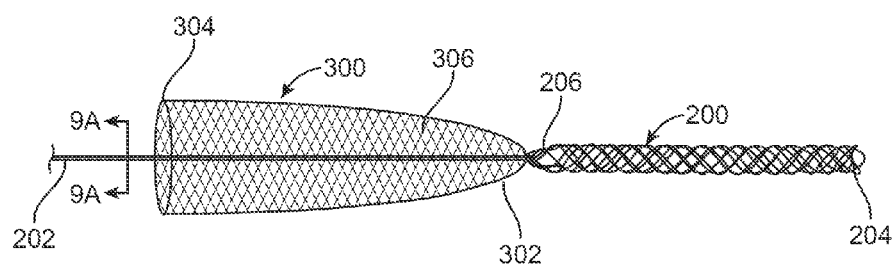
FIGS. 2A to 2C illustrate working ends of various coverable retrieval devices.

FIG. 2A illustrates a working end of a coverable retrieval device 100. Typically, the device includes a capturing or retrieval structure 200. In the illustrated example, the retrieval structure 200 comprises an elongated stent structure. However, unless specifically noted, the capturing structure can comprise any number of devices, including but not limited to a filter, an artherectomy device, a rotational cutter, an aspiration catheter.

The retrieval structure 200 is located at a distal end of a delivery wire 202. In one variation, the retrieval structure 200 can be permanently affixed to the delivery wire 200 by such methods including, but not limited to adhesive bonding, soldering, welding, polymer joining, or any other conventional method. In some variations, the retrieval device 200 can be formed from one or more wires forming the delivery wire 202 or shaft 202. The delivery wire 202 can have sufficient column strength such that it can axially advance and retract the device 100 within the vasculature as the physician manipulates a non-working end of the delivery wire 202 outside of the body. Accordingly, the delivery wire 202 should have a length that is sufficient to extend from the target area, e.g., the cerebral vasculature, to the entry point on the body. Alternatively, additional variations of the device 100 can allow for the use of a support member or catheter that positions the retrieval structure 200 as needed. Additional features of the retrieval structure 200 can be found in the commonly assigned patents and applications cited herein an incorporated by reference.

The coverable retrieval device 100 further includes a cover 300 (also referred to as a funnel or sheath) affixed relative to a proximal end 206 of the retrieval structure 200. By being affixed relative to a proximal end 206, a distal end 204 of the retrieval structure 200 can move relative to the cover 300 so that the cover 300 everts over the proximal end 206 of the structure 200 when the cover 300 is expanded within a vessel and as the structure 200 is withdrawn into the distal end 302 of the cover 300. This mechanism is discussed in detail below.

Figure 2B:
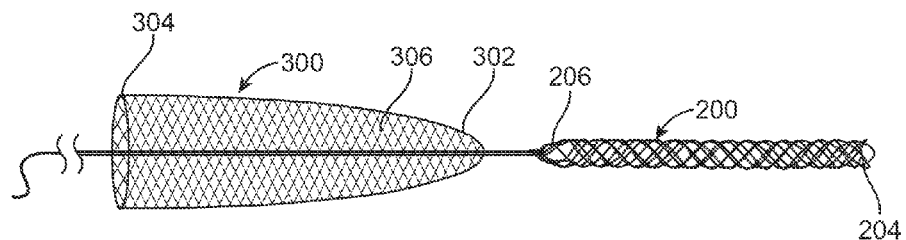
Figure 2C:
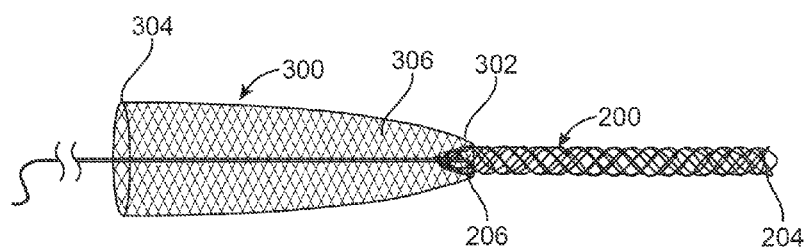

FIGS. 2B and 2C illustrate alternative variations of a coverable retrieval device 100. As shown in FIGS. 2B and 2C, the distal end 302 of the cover 300 can be spaced from the proximal end 206 of the retrieval structure 200. Alternatively, the distal end 302 of the cover 300 can extend over a portion of the retrieval structure 200. In some variations, at least a section of the cover 300 expands to a greater diameter than a diameter of the retrieval structure 200. This allows the cover 300 to expand to a vessel wall where the vessel holds the cover stationary while the device is pulled proximally through the cover to evert the cover. In alternate variations, the cover 300 expands to the same or lesser diameter than the retrieval structure 200 or other device.

Figure 2D:
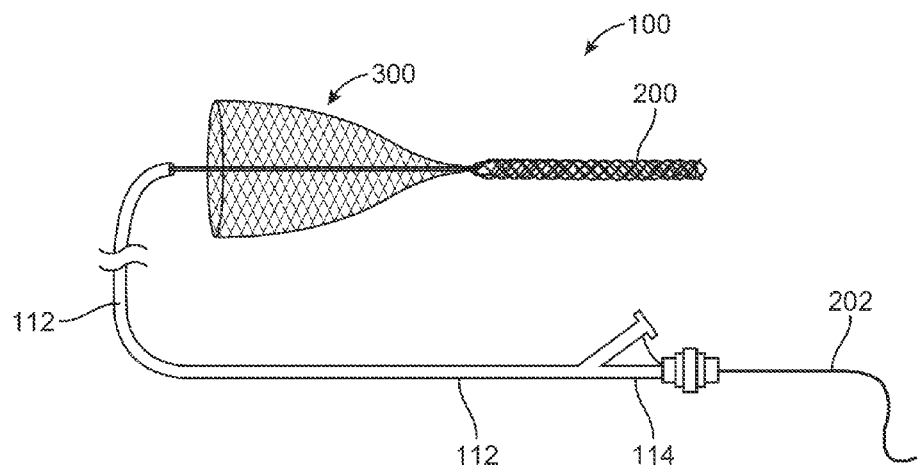
FIGS. 2D and 2E show variations of retrieval devices.

FIG. 2D shows a retrieval device 100 with a catheter 112 (usually a microcatheter). The retrieval device 100 can comprise a single unitary device of a cover 300 and retrieval structure 200 (in this case the retrieval structure is an elongated stent structure). One benefit of a unitary device is that additional devices complicates the procedure and can increase the duration of what is ordinarily a time sensitive procedure. The retrieval device 100 can be positioned through the catheter 112 that includes a hub 114. As a result, the physician only needs to manipulate the unitary retrieval device 100 and the catheter/microcatheter 112. The retrieval device 100 is loaded into the catheter 112 for placement at the target site. In addition, the retrieval device can be reloaded if the procedure must be repeated. The cover 300 and retrieval structure 200 described herein can comprise any construction described herein or as known by those skilled in the art.

Figure 2E:
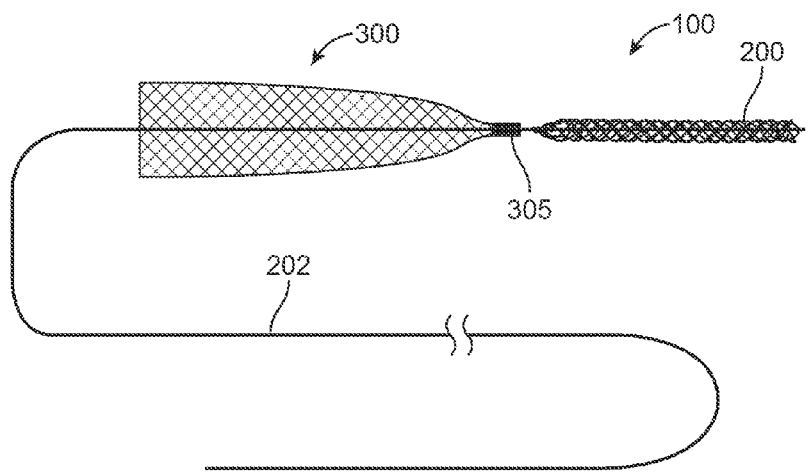

FIG. 2E shows a retrieval device 100 with a cover 300 and retrieval device 200 with a radiopaque marker 305 therebetween. As shown, variations of the device 100 do not require a catheter or microcatheter.

Figure 2F:
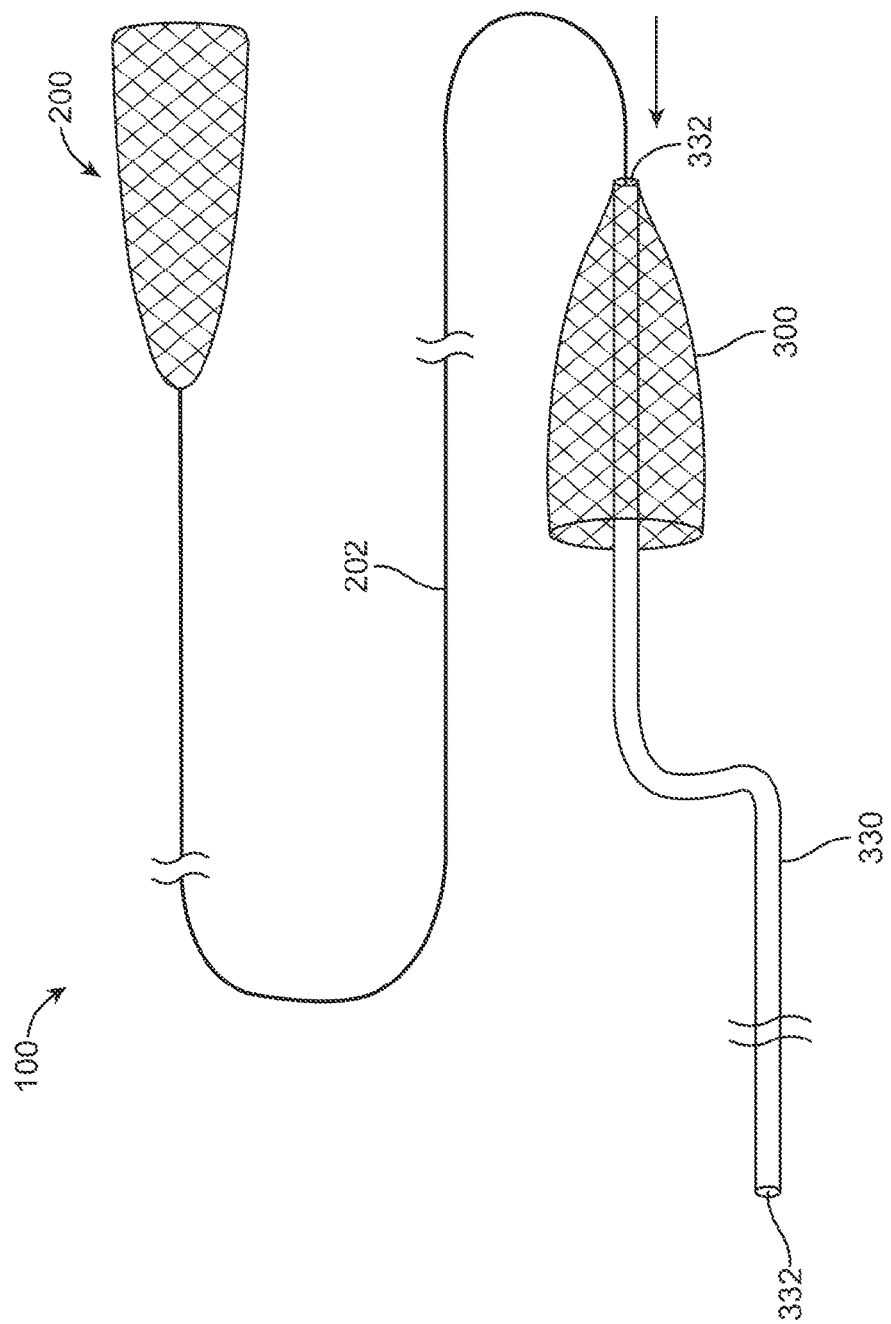
FIG. 2F shows an independent eversible cover on a delivery sheath.

FIG. 2F illustrates an eversible cover 300 located on a sheath 330 having a lumen 332 extending therethrough. A separable retrieval device 200 can be coupled to the cover 300 and sheath 330 by inserting the wire 202 of the cover retrieval device 200 through the lumen 332 of the sheath 330. In this variation, the eversible cover 300 can be used with any number of different interventional tools. The separate devices can be assembled prior to delivery into the patient. Alternatively, the devices can be positioned within the body and subsequently joined once the retrieval device 200 engages the target area.

Figure 3A:
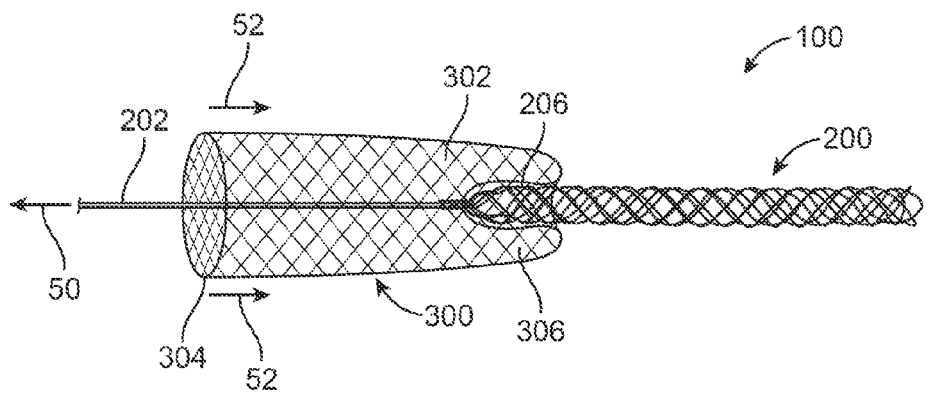
FIGS. 3A to 3C illustrate an example of a coverable retrieval device where the cover everts about the retrieval structure.
Figure 3B:
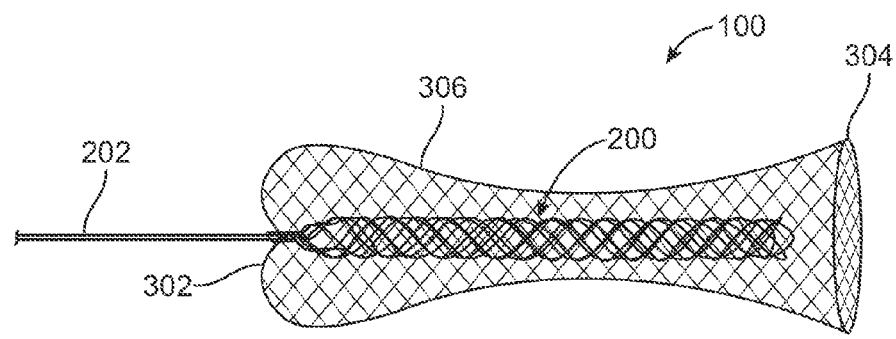

FIG. 3A illustrates an example of a coverable retrieval device 100 where the cover 300 is in the process of everting about the retrieval structure 200. As shown, arrow 50 illustrates a force applied on the wire 202 in a proximal direction. Arrows 52 illustrate a resistance force applied by the friction of the expanded cover 300 against a vessel or similar wall. This friction force 52 prevents or resists proximal movement of the free end 304 of the cover 300 while the fixed end 302 moves in a proximal direction with the proximal end 206 of the retrieval structure 200. This action causes a wall 306 of the cover 300 to evert over the retrieval structure 200. Ultimately, and as shown in FIG. 3B, the free end 304 of the cover 300 ends up distally over the fixed end 302. As shown, the wall of the everted cover 300 provides a safety type cover for the retrieval device 200. In additional variations, the fixed end 302 of the cover can actually be slidable or moveable along the delivery wire 202. However, the similar principle as discussed above shall apply to cause everting of the cover 300 over the retrieval structure 200.

Figure 3C:
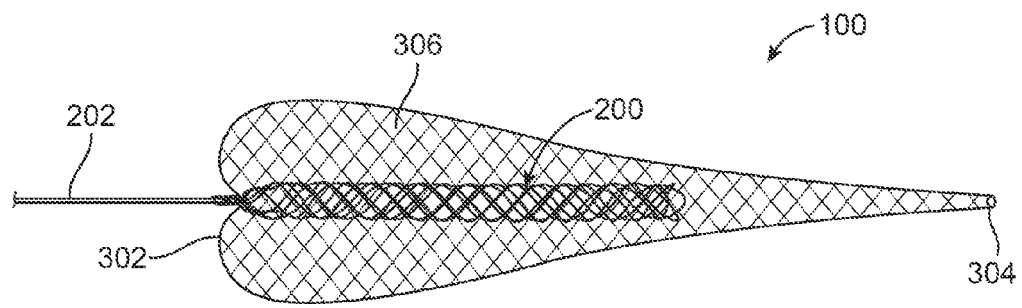

FIG. 3C illustrates another variation of a coverable retrieval device 100 after the cover 300 is everted about the retrieval structure 200. In this variation, the free end 304 of the cover 300 ends up distally of the fixed end 302 and tapers or collapses towards the free end 304. The cover 300 can be shape set so that prior to eversion the cover is as shown above where the forces acting on the cover wall 306 expand outwards, but after eversion the forces on the cover wall 306 cause the tapering or collapsing as shown in FIG. 3C.

In accordance with the illustrations discussed above, the cover 300 can be made so that the cover wall 306 is atraumatic when dragged across a lumen wall. The cover can be manufactured from any number of materials including a fabric, a reinforced fabric, a braid, weave, or any such material that allows for expansion against a wall of the body lumen or vessel as well as to allow everting of a wall 306 of the cover over the retrieval device 200. The cover wall 306 can also comprise combinations of these materials such as braids of polymer material with metal fibers, soft braids with coil reinforcements or various other combinations.

The cover wall can comprise a mesh that can include any medically acceptable materials such as a Nitinol braid. Furthermore, the mesh allows for flow through the vessel or lumen while expanded. However, additional variations of the device can include a solid layer of material substituted for the mesh. Moreover the cover can comprise any number of configurations. For example, the cover can comprise a single layer wall or a multi layer wall, the open end of the cover could be made to have terminated ends such as by using continuous wire loops formed during the braiding process. Alternatively, the ends can be cut and then terminated by encasing in polymer, laser welds, or by folding inward for a discreet length and then terminating In one example, the cover 300 comprises a continuous wire construction as described in earlier commonly assigned patent applications incorporated by reference. In one variation the cover 300 comprises a finely braided wire, such as 48-96 wires of 0.0005" to 0.002" diameter fine Nitinol wire or similar. Additionally, the wire can comprise cobalt chromium, stainless steel, or similar, or drawn filled tube (dft) with platinum core. In additional variations, a flat wire or oval wire can be used. The wire does not need to be uniform. Instead, a number of different types of wires can be used. Some of the individual wires could be platinum alloys for added radiopacity.

Figure 4A:
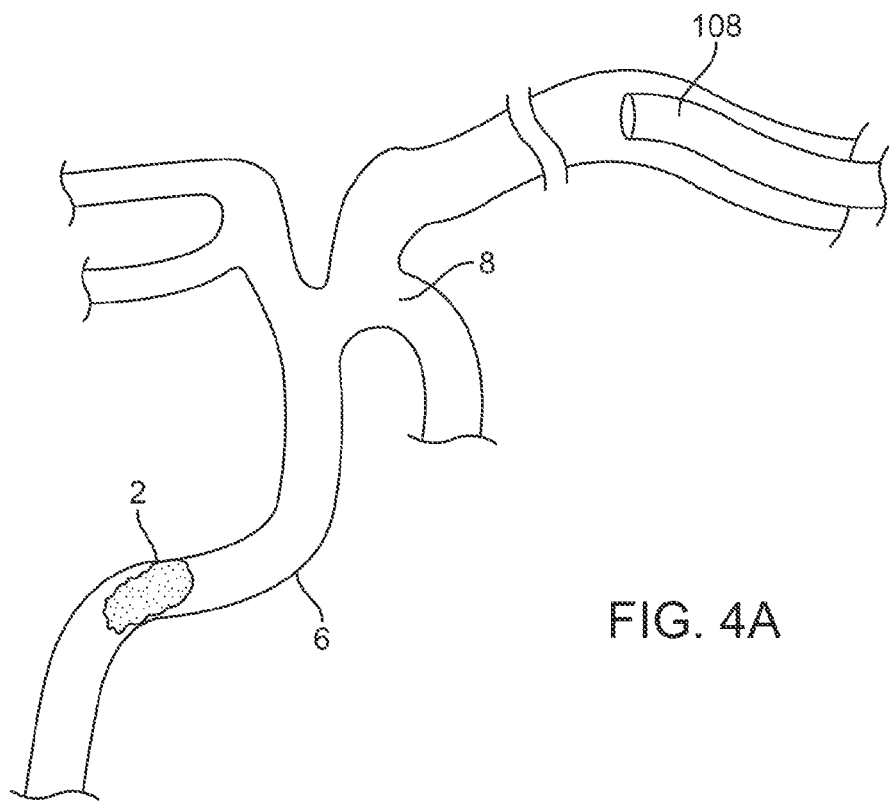
FIG. 4A to 4I illustrates an example where an improved retrieval device with passive protection retrieves a clot from tortuous anatomy.

FIG. 4A to 4I illustrates an example where an improved retrieval device 100 with passive protection retrieves a clot 2 from tortuous anatomy. FIG. 4A illustrates a clot 2 that obstructs blood flow in a vessel 6. As noted herein, the vessel 6 can comprise any vessel in cerebral vasculature, coronary or peripheral vasculature. Alternatively, the device and methods for use are not limited to use in the vasculature. Variations of the principles, concepts, method and devices described herein can be applicable wherever a retrieval device can be used. FIG. 4A also illustrates a guide sheath or access catheter 108 that is advanced within the vessel. During a procedure, the physician will advance the access catheter 108 as far distally as possible. However, due to the size of the access catheter 108, a physician typically positions it a distance away from the obstruction 2. As shown, there can be any number of bifurcations 8 in the vessel 6 located between the access catheter 108 and the obstruction 2. As discussed herein, in some variations, the access catheter 108 can be used to remove the obstruction 2 from the body once the obstruction is captured by a retrieval device. However, the greater the distance between the initial location of the obstruction 2 and the location of the access catheter 108, the greater the risk that the obstruction 2 can break free from the retrieval device or become dislodged due to anatomic or environmental features, including but not limited to bifurcations, the wall of the lumen, the tortuousity of the anatomy, vessel wall plaque, etc.

Figure 4B:
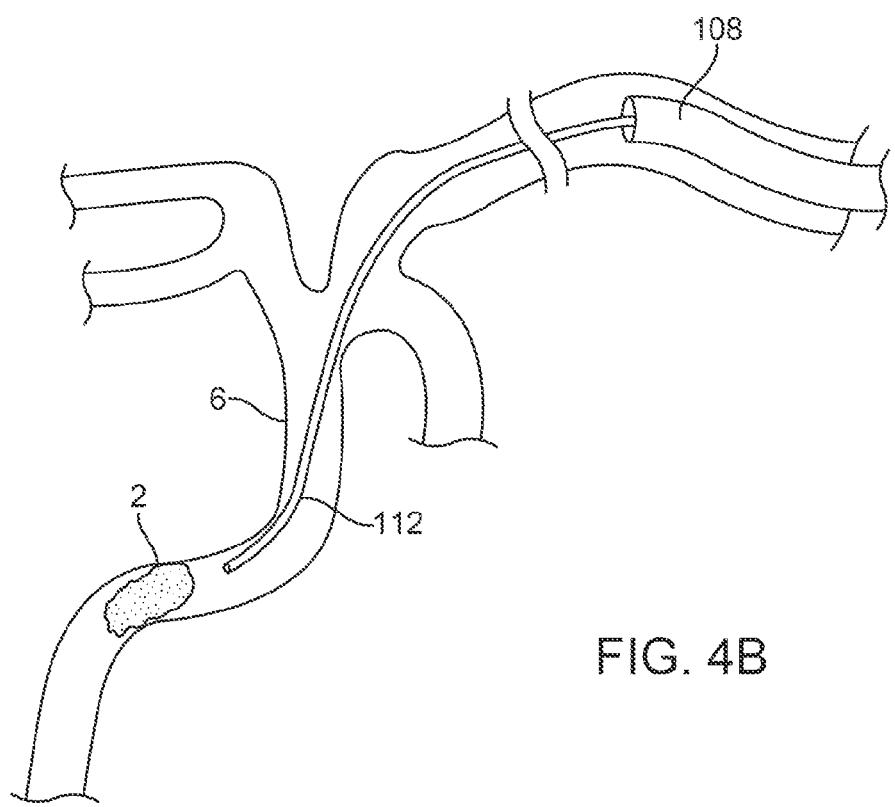
Figure 4C:
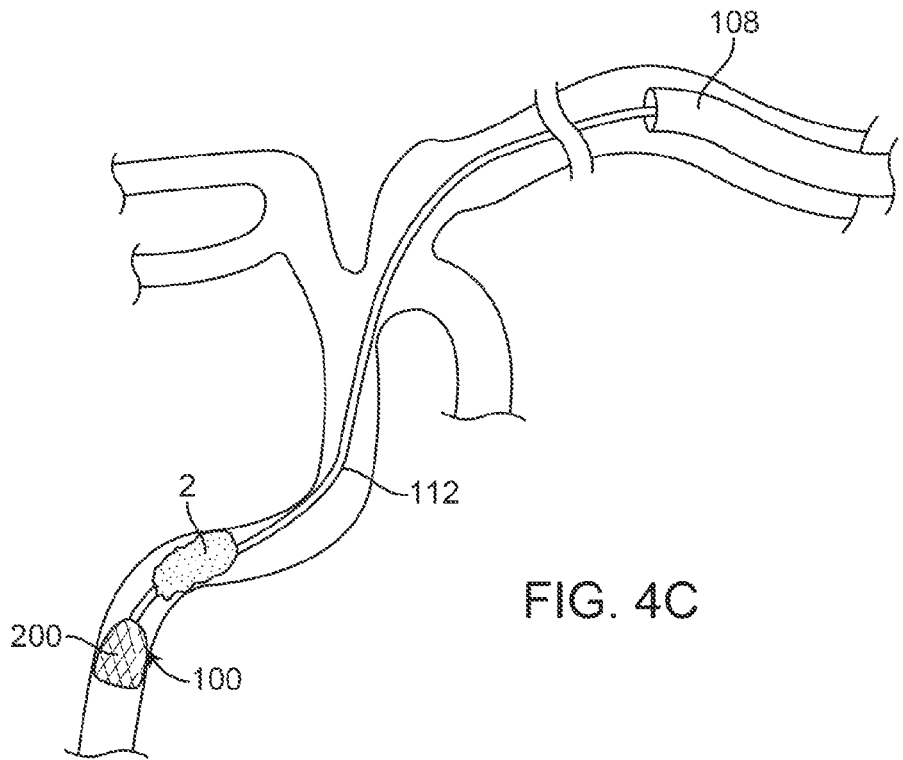
Figure 4D:
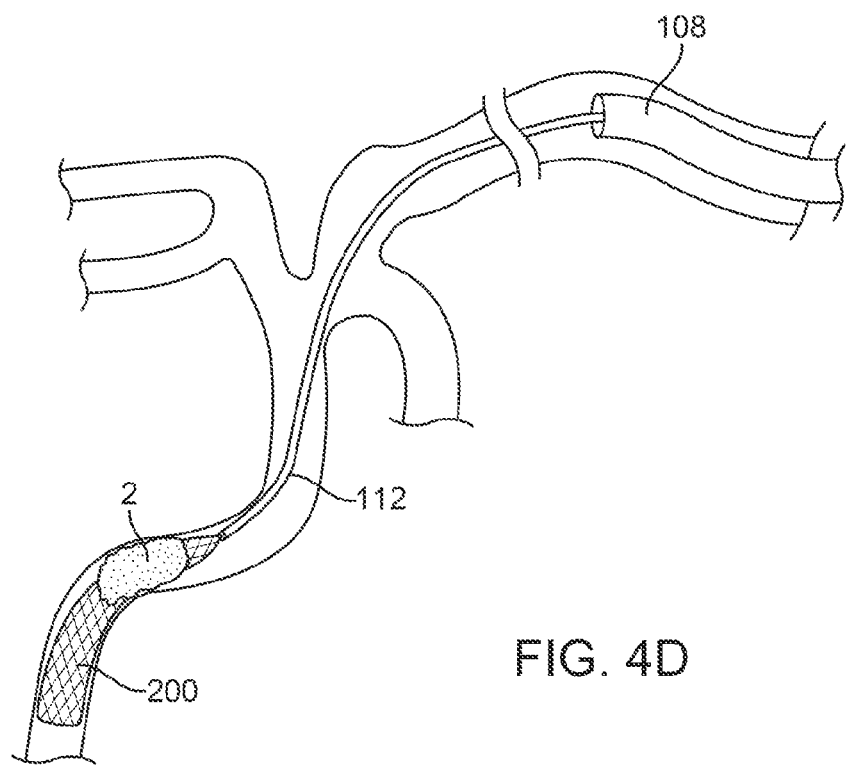

FIG. 4B illustrates an optional catheter 112 that advances from the access catheter 108 to the site of the obstruction 2. Once at the site, the catheter 112 can deploy a retrieval device (not shown in FIG. 4B) so that the retrieval device can engage the clot 2. Alternatively, the catheter 112 can traverse the obstruction 2 as shown in FIG. 4C and deploy a portion of the retrieval device 100 distally to the obstruction 2. The physician then manipulates the retrieval device 100 to secure the obstruction 2. For example, the physician can deploy the retrieval structure 200 distally to the obstruction 6 and withdraw the retrieval structure 200 proximally to secure the obstruction 2. In another variation, the physician can position the retrieval structure 200 within the catheter 2 while the catheter 112 is through or adjacent to the obstruction 2. Then, the physician can withdraw the catheter 112 to expose the retrieval structure 200 so that it secures to the obstruction 2 after expansion. In the illustrated example, the retrieval structure 200 comprises an elongated stent type structure that expands (or is expanded) to enmesh or secure to the obstruction. Although not illustrated, the system can include a distal capture filter or basket as described in any of the commonly assigned applications incorporated by reference herein.

Figure 4E:
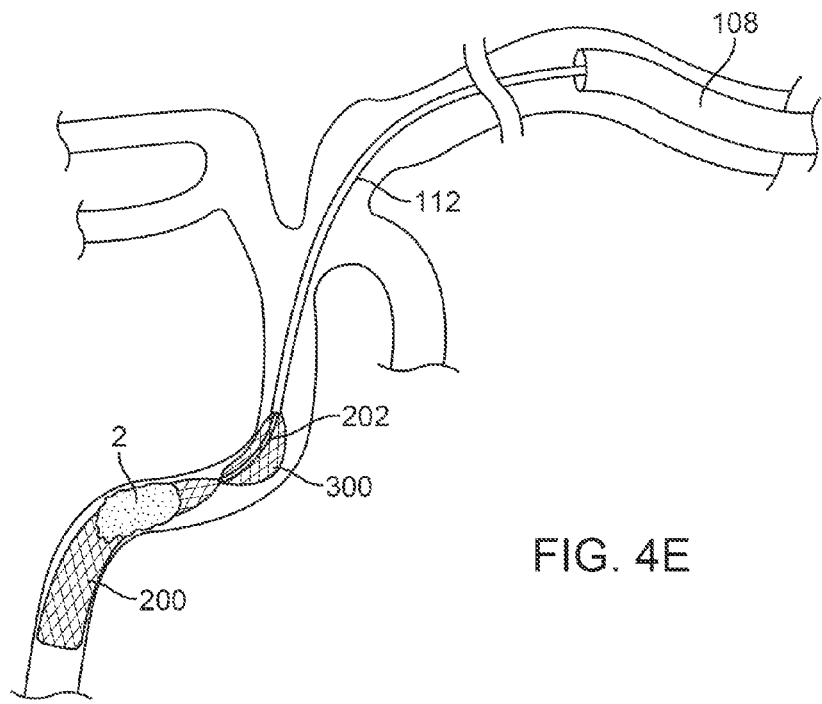

Next, as shown in FIG. 4E, the physician can further withdraw the catheter 112 to expose a cover 300 as described above. In many cases, the physician exposes the cove 300 once the retrieval structure 200 is engaged with the obstruction 2. This sequential process allows for easier repositioning of the retrieval structure 200 if necessary. Alternatively, the cover 300 can be deployed prior to engaging the retrieval structure 200 with the obstruction 2. If necessary, the physician can apply a proximal force on the delivery wire 202 while withdrawing the catheter 112 to prevent inadvertent movement of the obstruction 2 and retrieval device 200.

Figure 4F:
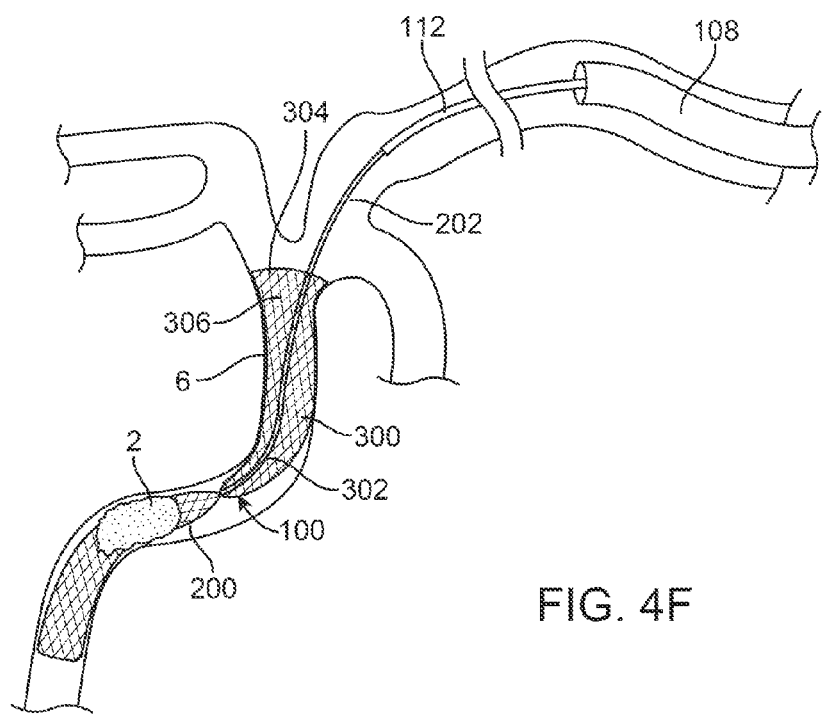

FIG. 4F illustrates the stage with a fully exposed the cover 300 and a catheter 112 moved closer towards the access sheath 108. As shown, the free end 304 of the cover 300 is proximal to fixed end 302 of the cover 300. As also noted above, the cover 300 can be a shape memory alloy that expands against the walls of the vessel 6 upon reaching body temperature. Alternatively, the cover 300 can be self expanding upon deployment into the vessel 6. In some variations, the cover wall 306 comprises a porous material or construction that allows blood to continue to flow through the cover 300.

In addition, some variations of the retrieval device 100 include a cover 300 that has at least a section that expands to a greater diameter or dimension than the retrieval structure 200. This allows for expansion of the cover 300 against the wall of the vessel 6. In most variation, expansion of the cover 300 provides sufficient friction against the walls of the vessel to overcome column strength of the cover walls 306 allowing for everting of the cover walls 306 over the retrieval structure 200 and obstruction 2 as discussed herein. As noted above, in alternate variations the cover 300 can expand a diameter or dimension that is equal to or less than the retrieval structure 200.

Figure 4G:
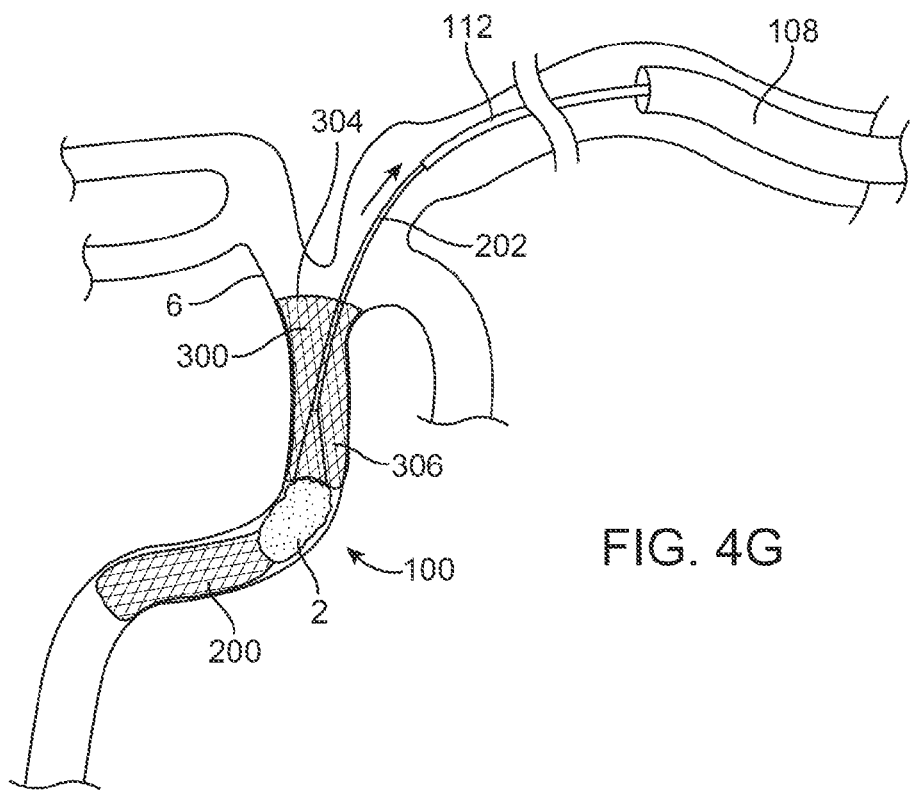

FIG. 4G illustrates proximal movement of the delivery wire 202, which causes proximal translation of the obstruction 2 and retrieval structure 200. Because the cover 300 is expanded against the walls of the vessel 6 the free end 304 of the cover 300 does not move or moves less than the fixed end 306 of the cover 300. The fixed end 306 moves with the obstruction 2 and retrieval structure 200 in a proximal direction causing the cover walls 306 to evert over the obstruction 2 and retrieval structure 200. Unlike a conventional funnel, the everting cover functions similar to a conveyor belt type movement as the obstruction and retrieval structure move together. This action allows for a passive type of protection since cover 300 does not need to be actuated over the obstruction 2 and retrieval structure 200 and can be performed in a quick manner by simply withdrawing the deployed retrieval device 100.

Figure 4H:
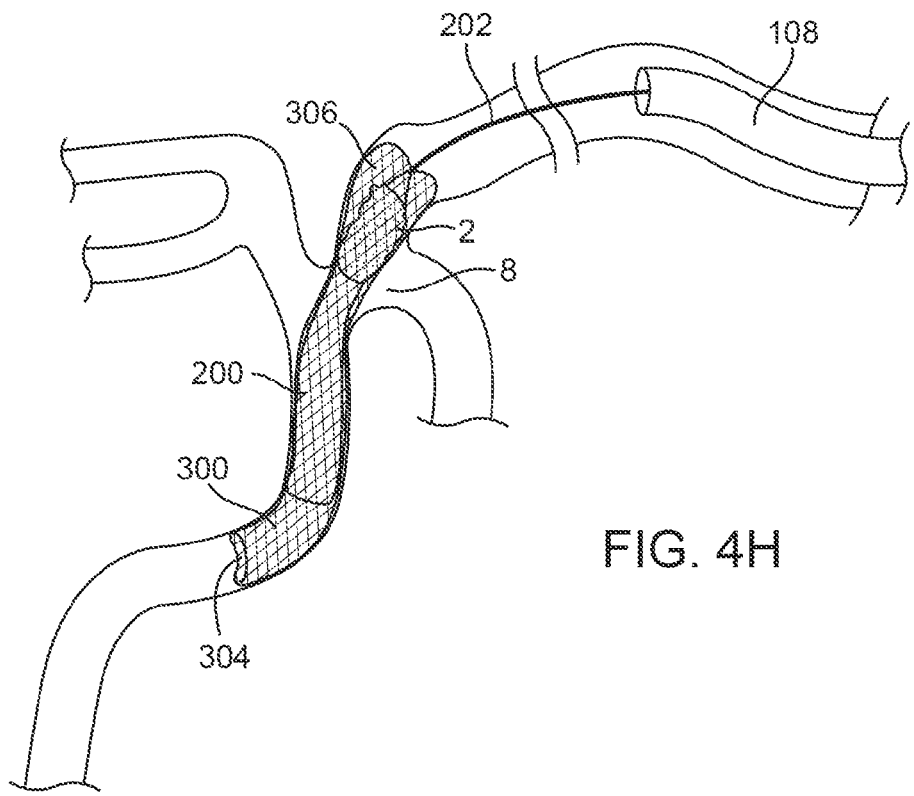

FIG. 4H illustrates a stage where the fixed end 306 of the cover 300 is now proximal to the free end 304. As shown, the everted cover 300 forms a protective sheath or cover over the obstruction 2 and the retrieval structure 200. FIG. 4H also illustrates how the cover 300 protects the obstruction 2 and retrieval structure 200 as they are pulled along the vessel and navigate the tortuous anatomy, walls of the vessel, as well as bifurcations 8. The cover 300 and cover wall 306 also protects the vasculature from the surface of the retrieval structure 200 and obstruction 2.

Figure 4I:
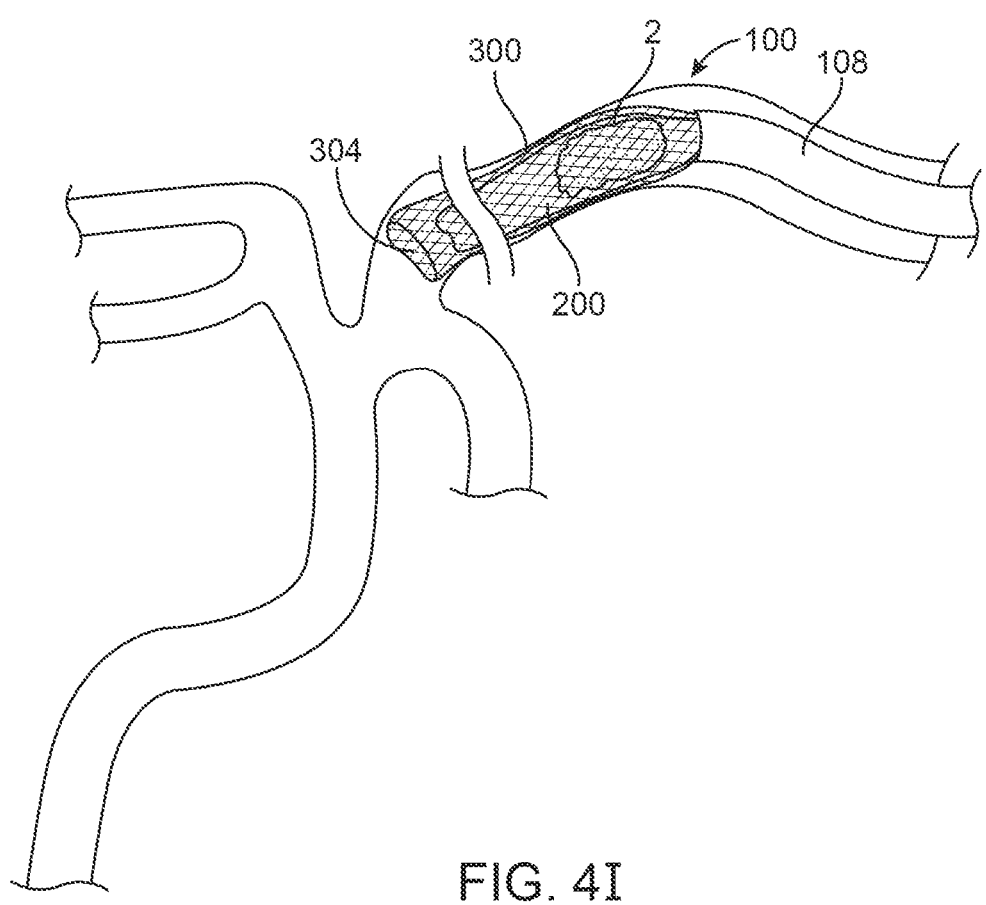

FIG. 4I shows the obstruction 2 and retrieval structure 200 protected by the cover 300 as the retrieval device 100 is positioned against or within the access catheter 108 in preparation for removal from the body. The retrieval device 100 can remain outside of the access catheter 108 as the physician removes both devices from the body. Alternatively, the cover 300 can assist in pulling the retrieval device 100 and obstruction 2 into the access catheter 108 by compressing the obstruction 2 as it is pulled into the access catheter 108.

FIGS. 4J and 4K illustrate examples of an obstruction or other material 2 captured within a retrieval device 2 with a cover 300 further protecting the loaded retrieval device 200.

Figure 5A:
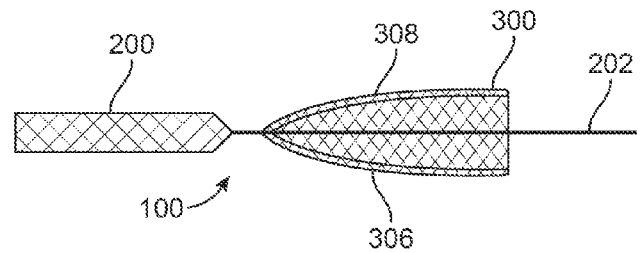
FIG. 5A illustrates a retrieval device having a retrieval structure adjacent to a double layer cover.

FIGS. 5A to 5K show a variety of cover configurations. FIG. 5A illustrates a retrieval device 100 having a retrieval structure 200 adjacent to a double layer cover 300 with an exterior wall 306 and an interior wall 308.

Figure 5B:
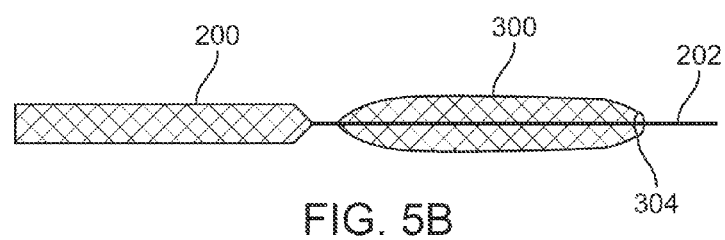
FIG. 5B shows a funnel with a free end that tapers down about the delivery wire.

FIG. 5B shows a cover 300 with a free end 304 that tapers down about the delivery wire 202 where the cover 300 will eventually form a double wall configuration when the cover 300 everts over the retrieval structure 200. The tapered free end 304 limits the cover 304 from moving once the retrieval structure 200 reaches the free end 304 thereby forming double wall protection over the retrieval structure 200.

Figure 5C:
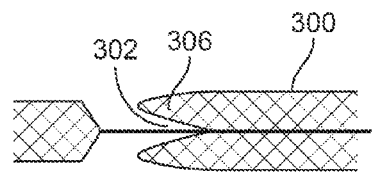
FIGS. 5C and 5D show a fixed end of a cover that is pre-shaped to reduce the force required to evert the cover wall.
Figure 5D:
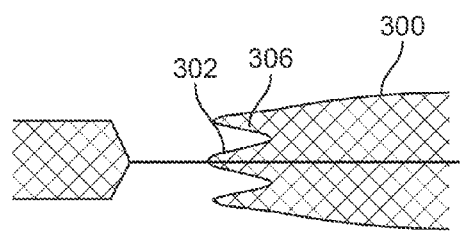

FIGS. 5C and 5D show how a fixed end 302 of a cover 300 can be pre-shaped to reduce the force required to evert the cover wall 306 or to lower the threshold to trigger passive covering of the retrieval structure by the cover.

Figure 5E:
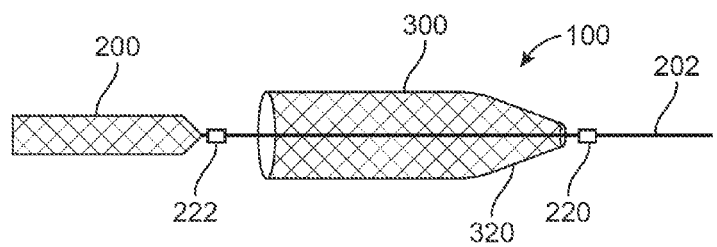
FIG. 5E shows alternate variation of a passive cover integrated into a retrieval device.

FIG. 5E shows alternate variation of a passive cover 300 integrated into a retrieval device 100. In this variation, the retrieval device 100 includes a control shaft or wire 202 to manipulate the working end of the retrieval device 100. The cover 300 floats along the shaft 202 between two fixed anchors or nodes 220, 222. The cover 300 can float or slide between the fixed nodes 220, 222. The nodes 220, 222 can comprise radiopaque marker bands, glue joints, or any other mechanical obstructions capable of stopping the translation of cover 300. When the device 100 advances through a microcatheter, the rear or proximal node 220 limits rearward movement of the cover 300. When positioned appropriately, the microcatheter can be withdrawn to expose the retrieval device 200 and cover 300 as described herein. When the retrieval structure 200 engages the obstruction (not shown) the retrieval device 100 can be withdrawn by pulling on the delivery shaft 202. While this occurs, the cover 300, being expanded against the vessel remains stationary (or moves at a slower rate than the obstruction and retrieval structure 200 due to the friction against the vessel wall). The retrieval structure 200 and clot enter the cover 300, causing the distal node 222 to make contact with the near end 320 of the cover 300. This contact causes the retrieval structure 200 and cover 300 to translate as an integrated unit. It should be appreciated that the cover could be a single layer or double layer cover, and could have any of the wire design variables and termination variables described herein.

Figure 5F:
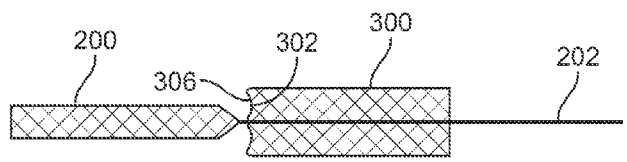
FIG. 5F illustrates a cover having a pre-set flattened cover wall at a fixed end of the retrieval structure.
Figure 5G:
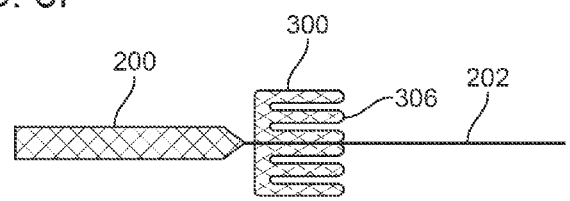
FIGS. 5G to 5I illustrate various layered covers.
Figure 5H:
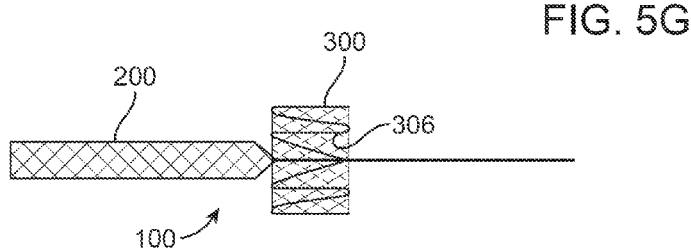
Figure 5I:
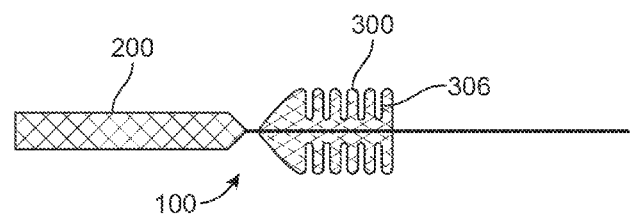

FIG. 5F illustrates a cover having a pre-set flattened cover wall 304 at a fixed end 302 that is spaced from a proximal end of the retrieval structure 200. FIGS. 5G to 5I illustrate various layered covers 300. The layered covers allow for shortening the axial length of the cover and therefore shortens the required translation length. Layering of the cover wall 306 allows for a shortened deployed length of the cover 300 when deployed in the vessel or body structure. As the cover 300 everts over the retrieval structure 200 the layered wall 306 extends. As a result, shortening the length reduces the length that the cover 300 extends into the proximal vessels and reduces the length of that the retrieval structure 200 must travel to become protected by the cover 300. This also helps shorten the distance required to move the device 100 to complete eversion of the cover 300.

Figure 5J:
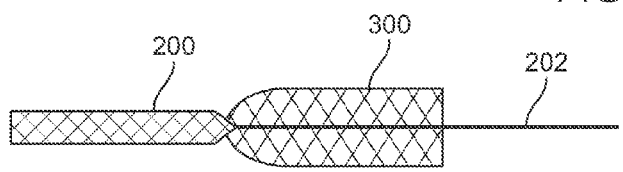
FIG. 5J shows a cover that is constructed directly onto the retrieval structure rather than the delivery shaft.

FIG. 5J shows a cover 300 that is constructed directly onto the retrieval structure 200 rather than the delivery shaft 202. This construction also assists in reducing the distance necessary to complete passive protection of the retrieval structure by the cover.

FIG. 5K show a variation of a cover 300 that is mounted in a distal direction over the retrieval device 200 and then everted in a proximal direction over the wires or shaft 202 as shown by arrows 230. Once everted, as shown by FIG. 5L, the device 100 is ready for deployment as discussed herein.

Figure 6A:
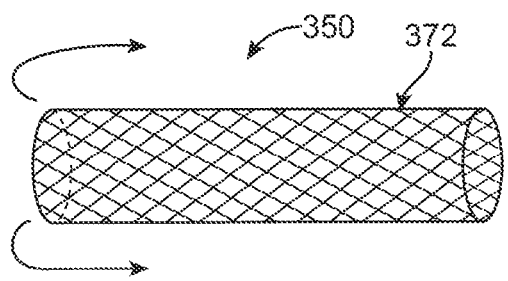
FIGS. 6A to 6L illustrate a variation of covers for use as describe herein.
Figure 6B:
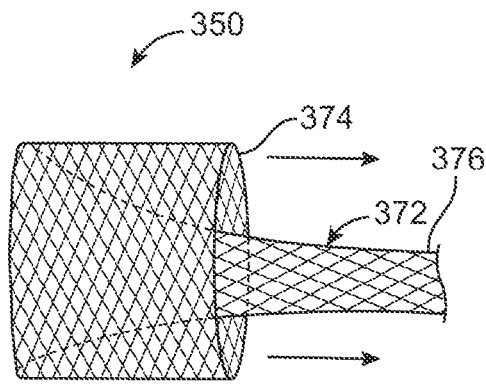

FIGS. 6A to 6B illustrate a variation of a cover 350 for use as describe herein. Additionally, the cover 350 can be used with any obstruction retrieval device not limited to the retrieval baskets and stents described herein. The covers 350 disclosed herein can be used where the physician desires to shield the obstruction being removed from the frictional effects of the arteries or from the local anatomy (e.g., branching vessels, tortuous anatomy, or other substances on the vessel walls). In use, the covers can be sized for use with guide catheters, micro-catheters, and/or distal access catheters. The covers can include any number of radiopaque marker bands to allow non-invasive imaging of the device (see marker 390 affixed between cover 350 and shaft 212 in FIG. 7B as one example). In any case, once the retrieval device captures a clot or obstruction, as described above, the device and clot are protected by the cover so that the cover eliminates or reduces direct contact between the interior of the wall of the vessel and the clot.

Figure 6C:
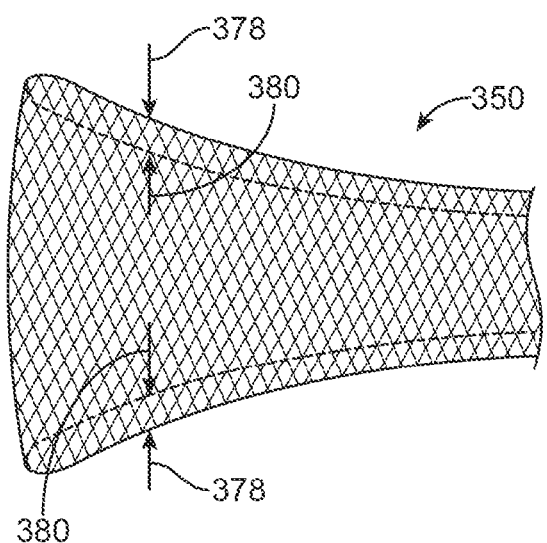
Figure 6D:
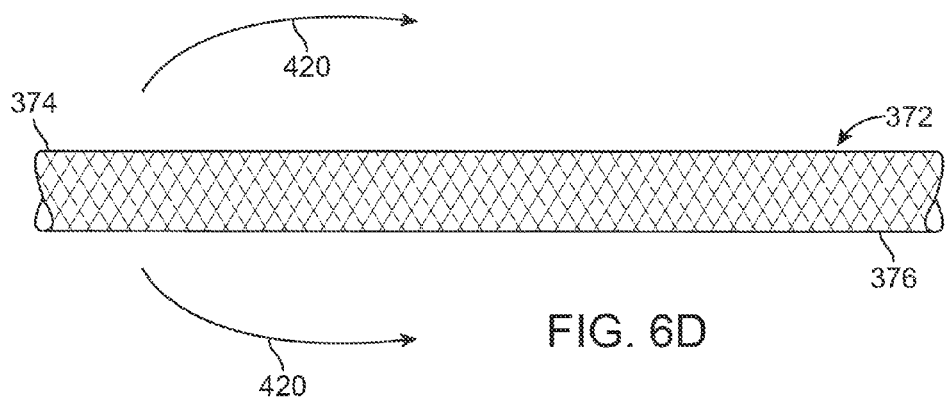

FIGS. 6A to 6C show a variation in which a cover is created from one or more mesh tubes 372. FIG. 6B illustrates inversion of the tube 372 so that a first end 374 is drawn over the tube 372 towards a second end 376. As shown in FIG. 6C, this creates a double walled cover having an exterior wall 378 separated from an interior wall 380. In one example, such a spacing or gap could range between 0.001 inches to 0.100 inches. However, any range is contemplated within alternative variations of the device. In some variations the inverted cover 350 is heat set to maintain a separation between layers or walls 378 380 of the cover 350. Typically, if the cover 350 is not created from a radiopaque material, a marker band will be placed on the proximal end 376 and adjacent to a shaft or catheter to which the cover 350 is attached. In some variations the construction of the mesh material is compliant to allow for movement of a first part of the mesh relative to a second part of the mesh through compression and expansion of the mesh material. In such a case, the individual strands forming the mesh are moveable relative to one another to cause the mesh to be naturally compliant. Accordingly, this construction permits the inner wall 380 to move or deflect with the retrieval device and/or obstruction as the device is withdrawn into the cover 350. In some variations, both ends of the mesh 374 and 376 are affixed to the catheter, shaft or wire.

In many variations, the cover mesh is selected to minimize friction when the interior layer 380 moves against the exterior layer 378. For example, the braid pattern, wire, wire diameter, angle of the braid and or other features can be selected to reduce friction between the outer layer 378 and inner layer 380. This permits the inner layer 380 to move proximally with a retrieval device while the outer layer remains stationary. Again, as discussed above, the construction of the mesh permits compression and expansion of the mesh layer to permit movement of the inner layer while the outer layer remains affixed when engaged against the vessel wall. In certain variations, the cover is heat set so that the inner layer has cushioning and the ability to deflect to assist in movement of the inner layer. FIG. 5C also illustrates a cover 350 having a tapered design.

Figure 6E:
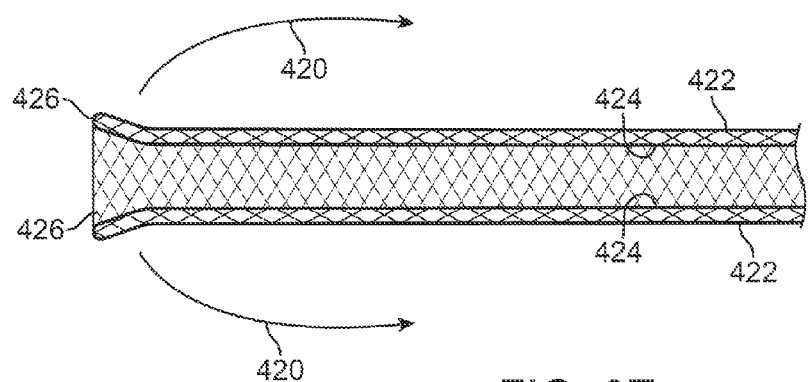
Figure 6F:
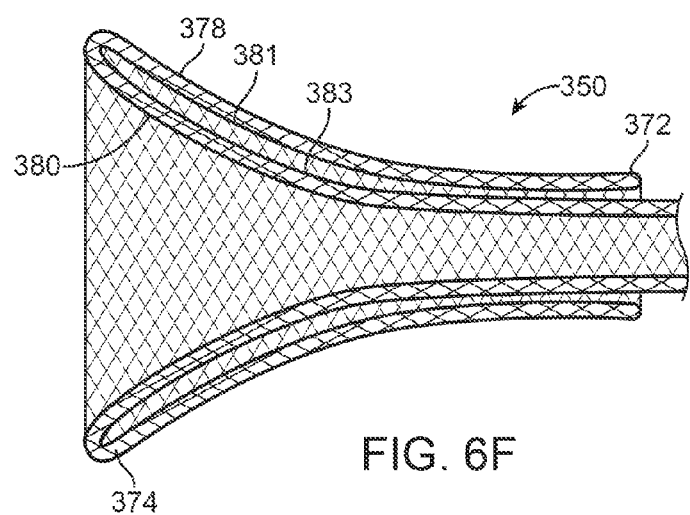

FIGS. 6D to 6L illustrate additional variations of cover construction to produce covers having more than two walls. For example, a mesh tube 372 is everted or drawn over a second end 376 in the direction 420. As shown in FIG. 6E this produces a dual layer cover having a open ends 422 and 424 and a folded end 426. The dual layer tube is then folded over again in the direction 420. This creates a cover construction with an exterior layer 378 and an interior layer 380 as well as a first intermediate layer 381 and a second intermediate layer 383. As shown in FIG. 6F, the cover can be set to assume the tapered shape having an opening at the first end 374 that is flared with the ends of the mesh at the second end 372, which are ultimately affixed to a shaft, wire or other catheter device as described herein.

Figure 6G:
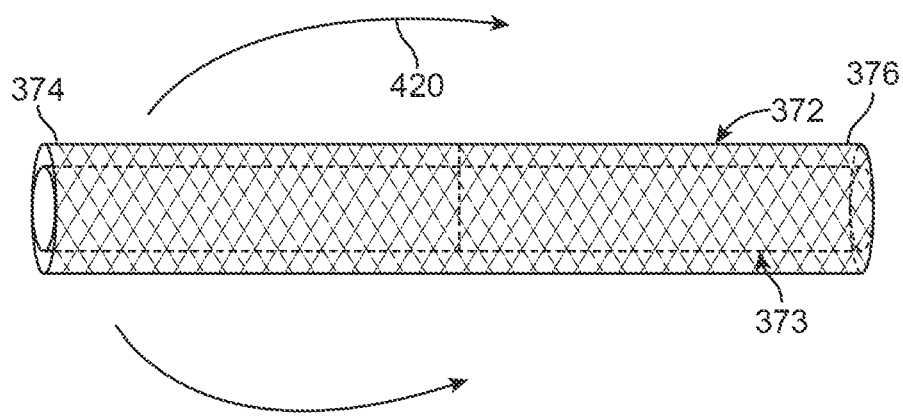
Figure 6H:
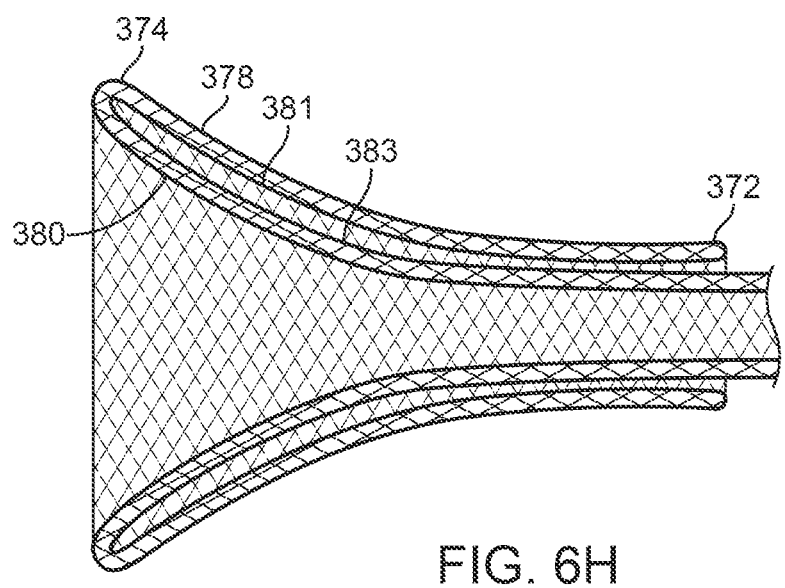

FIG. 6G illustrates another example of a cover construction. As shown, a first mesh tube 372 is placed coaxially with a second tube 372. The concentric tubes are then everted in direction 420 to produce a four layer cover. As shown in FIG. 6H, the cover can comprise an interior mesh layer 380, and exterior mesh layer 378 as well as any number of intermediate layers 381, 383 depending on the number of tubes that are initially used. The second end 372 of the cover 350 includes four unconnected ends of the mesh tubes that can be affixed to a shaft or tube as discussed herein, while the first end 374 of the cover 350 can be shape set to taper from the opening.

Figure 6I:
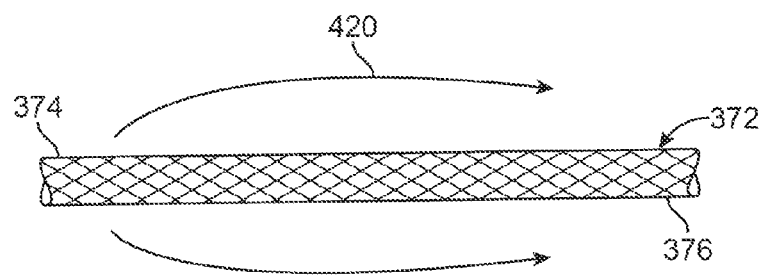
Figure 6J:
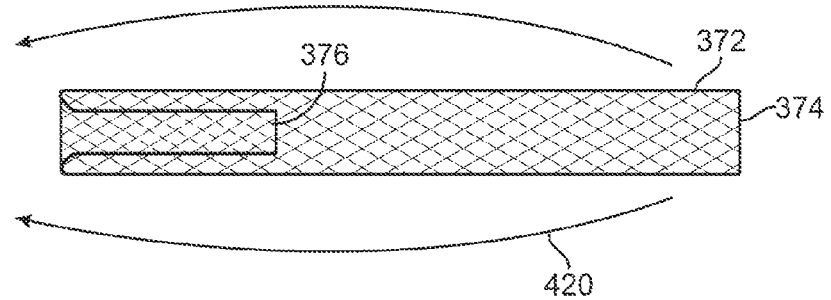
Figure 6K:
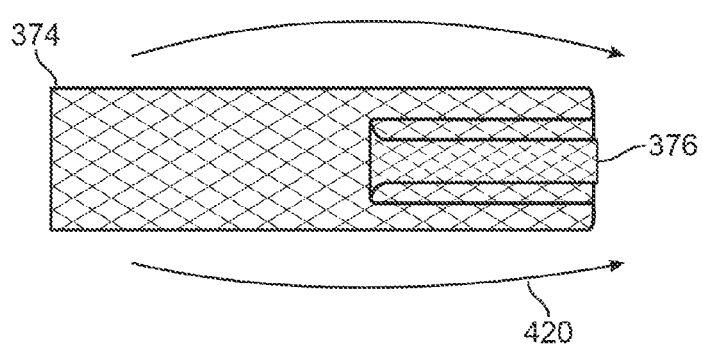
Figure 6L:
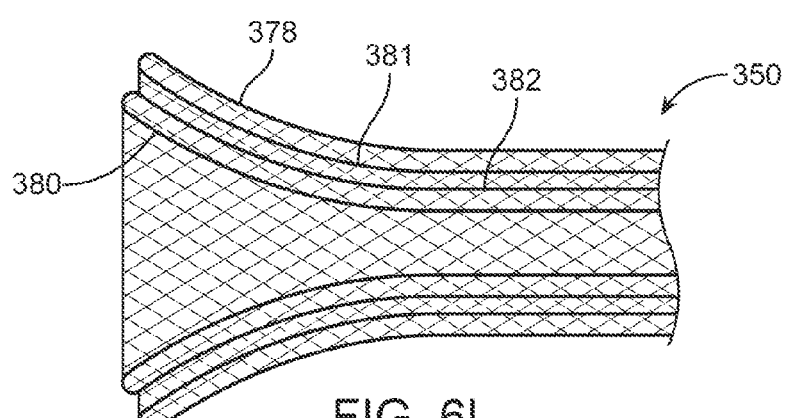

FIGS. 6I to 6L illustrate another example of the construction of a multi-wall cover. As shown in FIG. 6I, a first end 374 of a mesh tube 372 is everted over and beyond a second end 376 in direction 420 to produce the configuration of FIG. 6J. Next, the first end 374 is everted or folded back in direction 420 to produce the configuration of FIG. 6K. Finally, the first end 374 is folded again in direction 420 so that the ends 374 and 376 are even to produce the cover configuration shown in FIG. 6K. Again, one end of the cover 350 can be set to form the tapered shape while the other respective end can be affixed to a catheter or shaft.

Although the covers of the present disclosure are presented without additional structures, it should be noted that these covers are coupled with a shaft or other member so that the cover can be advanced within the target anatomy to assist in removal of a device, structure, or debris from the site.

Figure 7A:
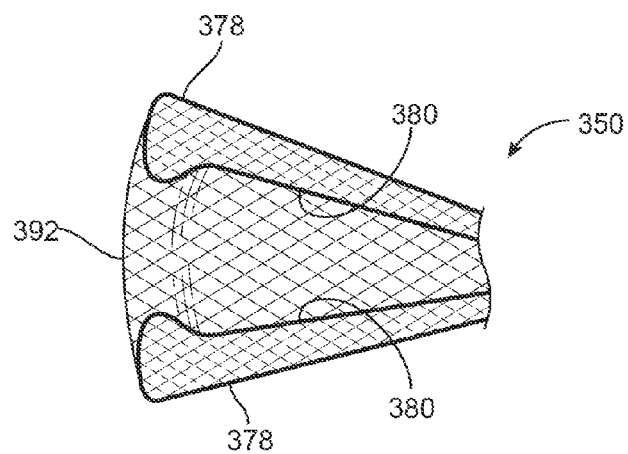
FIGS. 7A to 7C show additional variations of covers.
Figure 7B:
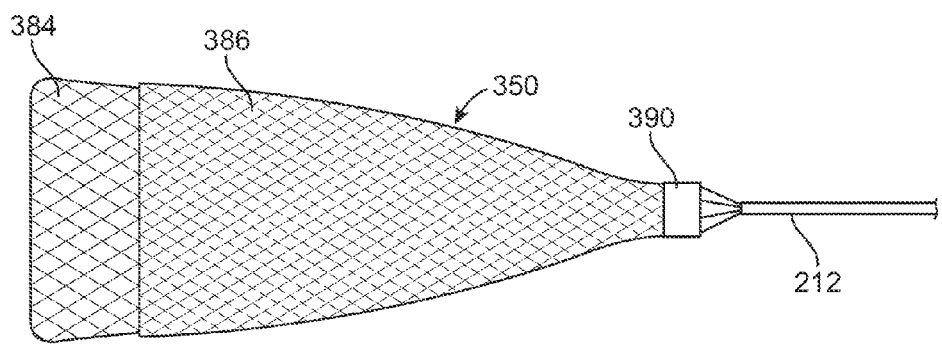
Figure 7C:
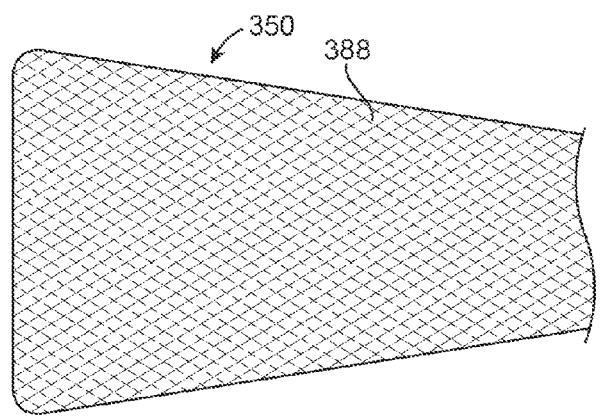

FIGS. 7A to 7C show addition variations of covers 350. FIG. 7A illustrates a cover in which the cover wall as defined by the inner layer 380 and outer layer 378 is set in a shape that varies along a length of the cover. For example, the end adjacent to the cover opening 382 can be set to a bulbous shape. Such a configuration assists in maintaining separation of layers 378 and 380, which aids in re-entry of the retrieval device. Additional configurations of cover walls that vary in thickness are within the scope of this disclosure.

One of the benefits of using a cover 350 as described herein is that the cover reduces flow through the vessel when deployed so that the retrieval device can remove the obstruction without the full force of the flow of blood opposing the obstruction. Typically, conventional devices relied upon the use of an inflated balloon to obstruct flow. However, use of a cover eliminates the need for total occlusion of blood flow. FIG. 7B illustrates a further improvement on a cover 350 that aids in flow reduction. As shown, the cover 350 includes a dense region 386 and a relatively less dense region 384. This configuration permits greater blood flow through the region 385 while region 386 reduces or prevents blood flow. Furthermore, the distal section of the cover is more flexible and conformable. Additional mesh layers can be added to any of the cover designs to alter flow characteristics or even provide reinforcement to the cover. Alternatively, or in combination, the braid density can be altered to adjust the porosity of the braid at different sections. Furthermore, additional braid layers can also be used to affect porosity of portions of the cover or even the entire cover. Deployment of a cover can reduce blood flow by 30% to 40%. Adding additional layers or coatings can additionally reduce flow.

FIG. 7C shows another variation of a cover 350 in which the mesh partially or totally is obscured using a polymeric coating 388 that reduces the permeability of the mesh design. Furthermore, drugs or other substances can be placed within the cover wall of any of the covers or can be deposited on the cover using the polymeric coatings. In some examples, the covers described herein can range from a length of 10 mm up to 50 mm. The OD at the opening of the cover can range from 7 mm and could range between 4 mm to 10 mm. Again, any range of dimensions is contemplated within the disclosure.

The covers described herein can further be stacked on a device. For example, two or more covers can be placed on a device to provide added protection.

The cover/rentry devices described herein can be constructed of any material currently used in vascular applications, including those discussed above. Furthermore, fabrication of the cover from a DFT material can provide additional benefits as the entire cover remains radiopaque and can be imaged non-invasively. Furthermore, the covers can be provided with any type of medicament or bioactive substance either in a polymer that coats the mesh or in a delivery agent within the mesh or between layers. Such substances include tpa, urokinase, IIb/IIIa inhibitors, and other clot disruptors or inhibitors.

Figure 8:
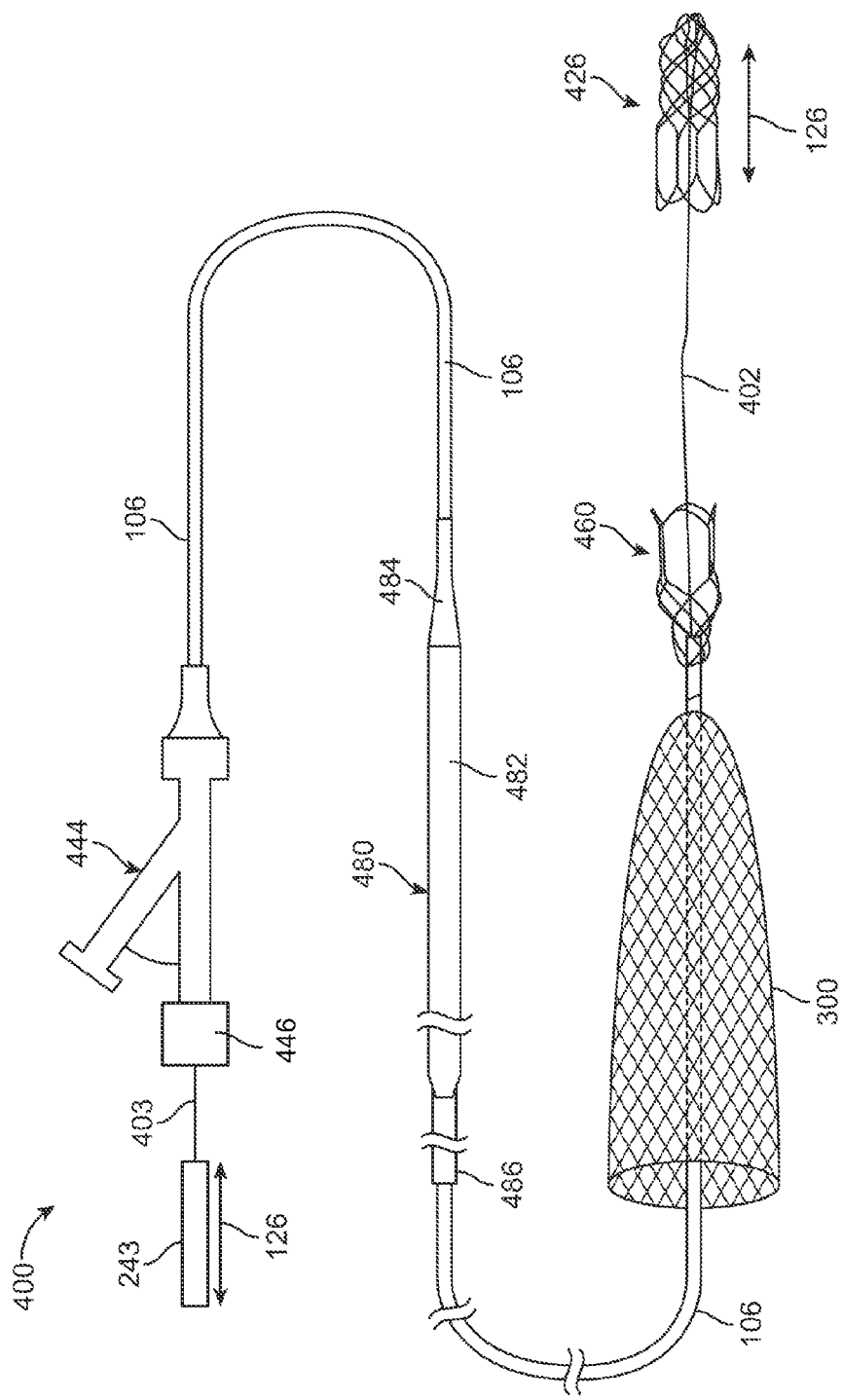
FIG. 8 illustrates a variation of a proximal and distal end of an additional retrieval device.

FIG. 8 illustrates another variation of a retrieval device 400 including a distal capture portion 426 coupled to one or more leading wires in the form of a main bundle 402. The main bundle extends through a sheath 106 that includes a proximal capture portion 460. The configuration of the retrieval device 400 can incorporate the proximal and distal capture portions discussed herein as well as various other configurations discussed in the commonly assigned patent applications noted above.

An end 464 of the proximal capture portion 460 is affixed to a distal end of the sheath 106. However, as noted above, other variations are within the scope of the disclosure. The main bundle 402 can optionally terminate at a handle 442. As noted above, in certain variations, the main bundle is joined to a stiffer wire or stiffer bundle of wires. This allows the device 400 to have a very flexible distal section with a relatively stiffer proximal section. The device 400 can have a proximal bundle 403 that comprises either the exposed wires or a covering/tube over the wires. In certain variations, the bundle or wire 402, 403 can be encapsulated with a coating. The device also includes a cover 300 adjacent to the retrieval device.

The proximal end of the sheath 106 includes a sheath handle 444. As discussed herein, axial movement of the bundle 402 or proximal bundle 403 (typically at the handle 442) results in movement 126, or translation of the bundle within the sheath 106. This action moves the distal capture portion 426 (as shown by arrows 126). In certain variations, the device 400 is loaded into a microcatheter (not shown but discussed above) that is delivered to the site of the obstruction and crosses the obstruction.

In some variations, the sheath hub 444 includes one or more locking hubs 446. Where actuation (either axial or rotational) of the locking hub 446 locks the main bundle 402 relative to the sheath handle 444 and sheath 106. It follows that such locking action also locks the distal capture portion 426 relative to the proximal capture portion 460. A variety of methods can be employed to increase a frictional interference between the locking hub 446 and the proximal bundle 403. As a result, when a physician determines a length of an obstruction, the physician can set a spacing between the capturing portions 426 460 by locking the proximal bundle 403 relative to the sheath hub 444. Accordingly, the proximal bundle 403 can include any type of incremental markings to allow the physician to readily determine a spacing of the capturing portions. As illustrated, the sheath hub 444 can include additional injection ports to deliver fluid or other substances through the sheath 106.

As noted above, the device 400 can be used with a micro-catheter. In those variations it is important that the device 400 is loaded without damaging the distal bundle 402, capture portions 426 460, and/or sheath 106. As a result, the device 400 can include an optional cover 486 that reduces the proximal capture portion 460 (and/or the distal capture portion 426) for loading within the microcatheter and/or sheath 106.

Another variation of the device 400 includes an insertion tool 480 slidably affixed to the sheath 480. Because variations of the device 400 can be extremely flexible, the insertion tool 480 can be used to provide column strength to the sheath 106, bundle 402 or other components as the device 400 is pushed into the microcatheter. The insertion tool comprises a rigid section 482 and a frictional coupler 484. The rigid section 282 has a column strength that supports the device 400 to prevent buckling. The frictional coupler 484 can be a flexible material that allows an operator to squeeze or grip the coupler 484 to create a temporary frictional interface between the loading tool 480 and the device 400 (typically the sheath 106). Such an action allows axial advancement of the device 400 as the loading tool 480 is advanced into the microcatheter. Once the rigid section 482 is fully inserted into the microcatheter, the operator releases the frictional coupler 484 and can withdraw the loading tool 480 from the catheter without withdrawing the device 400. The insertion tool 480 can also include an optional loading tube 486 slidably coupled to the rigid section 482. When used, the cover 486 can withdraw the proximal and distal capturing portion 226 260 within the loading tube 486. The loading tube 486 then couples to a microcatheter allowing the capturing portions to advance therein as the rigid section 482 and frictional coupler 484 advance the device 400 relative to the loading tube 486.

FIGS. 9A to 9C show cross sectional views taken along the line 9A-9A in FIG. 2A. As shown, the wire form construction described herein allows for a number of configurations depending on the particular application. For example, the individual wires 254 (as discussed herein) may themselves comprise a bundle of smaller wires or filaments. In addition, the wires can be selected from materials such as stainless steel, titanium, platinum, gold, iridium, tantalum, Nitinol, alloys, and/or polymeric strands. In addition, the wires used in a device may comprise a heterogeneous structure by using combinations of wires of different materials to produce a device having the particular desired properties. For example, one or more wires in the device may comprise a shape memory or superelastic alloy to impart predetermined shapes or resiliency to the device. In some variations, the mechanical properties of select wires can be altered. In such a case, the select wires can be treated to alter properties including: brittleness, ductility, elasticity, hardness, malleability, plasticity, strength, and toughness.

The device may include a number of radiopaque wires, such as gold and platinum for improved visibility under fluoroscopic imaging. In other words, any combination of materials may be incorporated into the device. In addition to the materials, the size of the wires may vary as needed. For example, the diameters of the wires may be the same or may vary as needed.

In addition, the individual wires may have cross-sectional shapes ranging from circular, oval, d-shaped, rectangular shape, etc. FIG. 9A illustrates one possible variation in which a number of circular wires 254 are included around another larger wire 256. Moreover, the device is not limited to having wires having the same cross-sectional shape or size. Instead, the device can have wires having different cross-sectional shapes. For example, as shown in FIG. 9B, one or more wires 256 can have a different cross-sectional shape or size than a reminder of the wires 254. Clearly, any number of variations is within the scope of this disclosure. This construction can apply to the retrieval portion, capturing portion and/or the covering portion of the device.

To illustrate one such example, a device can have 8-12 wires made of 0.003" round superelastic material (e.g., Nitinol). The device may additionally have 2-4 wires made from 0.002" platinum for fluoroscopy. Of the 8-12 Nitinol wires, 1-4 of these wires can be made of a larger diameter or different cross-section to increase the overall strength of the device. Finally, a couple of polymer fibers can be added where the fibers have a desired surface property for clot adherence, etc. Such a combination of wires provides a composite device with properties not conventionally possible in view of other formation means (such as laser cutting or etching the shape from a tube or joining materials with welds, etc.). Clearly, any number of permutations is possible given the principles of the invention.

In another example, the device may be fabricated from wires formed from a polymeric material or composite blend of polymeric materials. The polymeric composite can be selected such that it is very floppy until it is exposed to either the body fluids and or some other delivered activator that causes the polymer to further polymerize or stiffen for strength. Various coatings could protect the polymer from further polymerizing before the device is properly placed. The coatings could provide a specific duration for placement (e.g., 5 minutes) after which the covering degrades or is activated with an agent (that doesn't affect the surrounding tissues) allowing the device to increase in stiffness so that it doesn't stretch as the thrombus is pulled out. For example, shape memory polymers would allow the device to increase in stiffness.

In another variation, one or more of the wires used in the device may comprise a Drawn Filled Tube (DFT) such as those provided by Fort Wayne Metals, Fort Wayne, Ind. As shown in FIG. 9C, such a DFT wire 252 comprises a first material or shell 258 over a second material 260 having properties different from the outer shell. While a variety of materials can be used, one variation under the present devices includes a DFT wire having a superelastic (e.g., Nitinol) outer tube with a radiopaque material within the super-elastic outer shell. For example, the radiopaque material can include any commercially used radiopaque material, including but not limited to platinum, iridium, gold, tantalum, or similar alloy. One benefit of making a capturing portion from the DFT wire noted above, is that rather than having one or more markers over the capturing portion, the entire capturing portion can be fabricated from a super-elastic material while, at the same time, the super-elastic capturing portion is made radiopaque given the core of radiopaque material within the super-elastic shell. Clearly, any composite DFT wire 252 can be incorporated into the system and capturing portions described herein.

Another aspect applicable to all variations of the devices is to configure the devices or portions thereof that engage the obstruction to improve adherence to the obstruction. One such mode includes the use of coatings that bond to certain clots (or other materials causing the obstruction.) For example, the wires may be coated with a hydrogel or adhesive that bonds to a thrombus. Accordingly, as the device secures about a clot, the combination of the additive and the mechanical structure of the device may improve the effectiveness of the device in removing the obstruction. Coatings may also be combined with the capturing portions or catheter to improve the ability of the device to encapsulate and remove the obstruction (e.g., a hydrophilic coating).

Such improvements may also be mechanical or structural. Any portion of the capturing portion can have hooks, fibers, or barbs that grip into the obstruction as the device surrounds the obstruction. The hooks, fibers, or barbs 370 can be incorporated into any portion of the device. However, it will be important that such features do not hinder the ability of the practitioner to remove the device from the body.

In addition to additives, the device can be coupled to an RF or other power source (such as 14 or 16 in FIG. 1), to allow current, ultrasound or RF energy to transmit through the device and induce clotting or cause additional coagulation of a clot or other the obstruction.

Figure 10A:
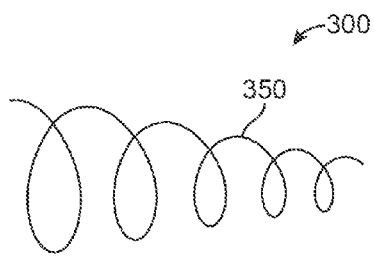
FIGS. 10A to 10E illustrate additional variations of covers for use as described above.
Figure 10B:
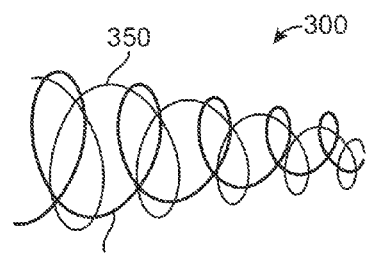
Figure 10C:
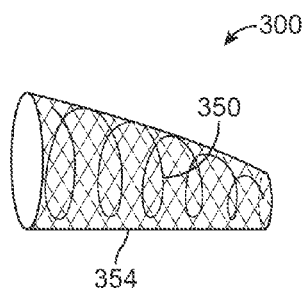
Figure 10D:
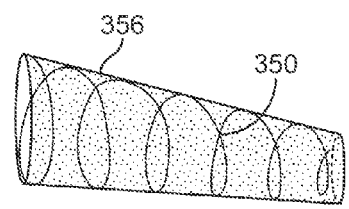
Figure 10E:
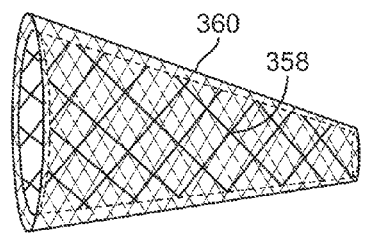

FIGS. 10A to 10E illustrate additional variations of covers 300 for use as described above. For example, as show in FIG. 10A, a cover 300 can comprise a single wire, coil, or laser cut tube 350. Alternatively, as shown in FIG. 10B, the cover 300 can comprises two or more 350, 352 wires or coils. FIG. 10C shows a cover 300 comprising a coil 350 inside a mesh structure 354. A variation of the device shown in FIG. 10C can include a compliant atraumatic mesh 354 that is radially supported by the coil (whether interior or exterior to the mesh). The coil 350 provides the outward force against the vessel. FIG. 10D illustrates a polymeric film or membrane 356 coupled to a coil 350. The polymeric film 356 can be permeable to fluid flow or impermeable. FIG. 10E illustrates a dual layer braid construction having an inner braid 358 and an outer braid 360. The braids can be constructed to have unique properties. For example, the inner braid 358 can be composed of fewer wires or larger diameter wires, such that it provides an expansion force against the vessel wall. The outer braid 360 can comprise a softer construction and increased compliance. Accordingly, it can be comprised of a number of smaller diameter wires having a denser pattern to provide increased surface area to protect the obstruction as it is removed from the body. Alternatively, these two constructional elements (e.g., braids of varying diameters) can be combined into a single layer or even multiple layers for the cover.

Figure 11A:
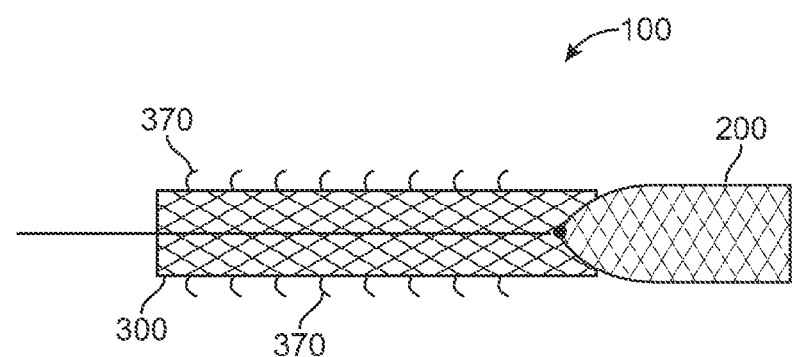
FIGS. 11A to 11C illustrate additional variations of covers for use with the devices and methods described herein.

FIG. 11A illustrates yet another variation of a device 100 having a retrieval structure 200 and cover 300 where the cover is simply fabricated from the same material as the retrieval structure so long as it functions as described herein. The variation can optionally include one or more barbs 370 to increase resistance against a vessel wall.

Figure 11B:
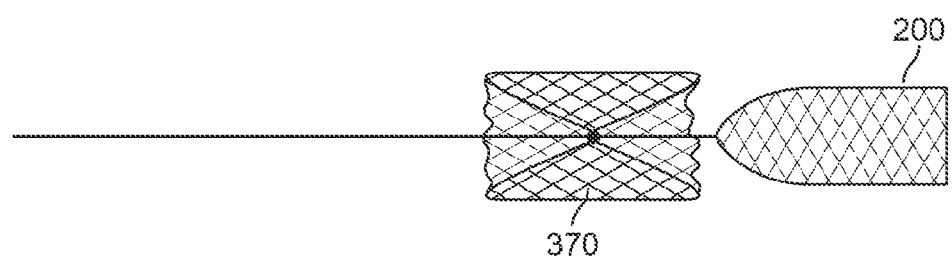
Figure 11C:
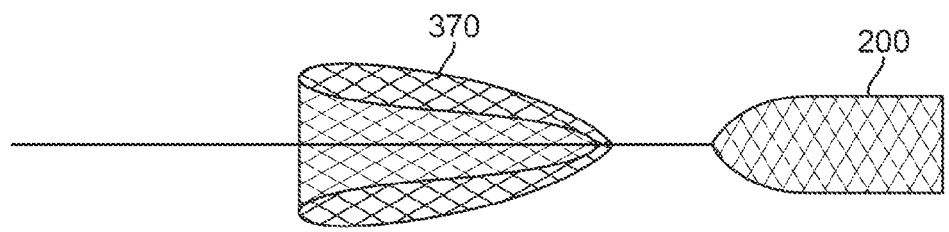

FIGS. 11B and 11C illustrate a variation where the cover 300 comprises a balloon material. FIG. 11B illustrates the balloon cover 370 prior to deployment. FIG. 11C illustrates the balloon cover 370 once deployed.

Figure 12A:
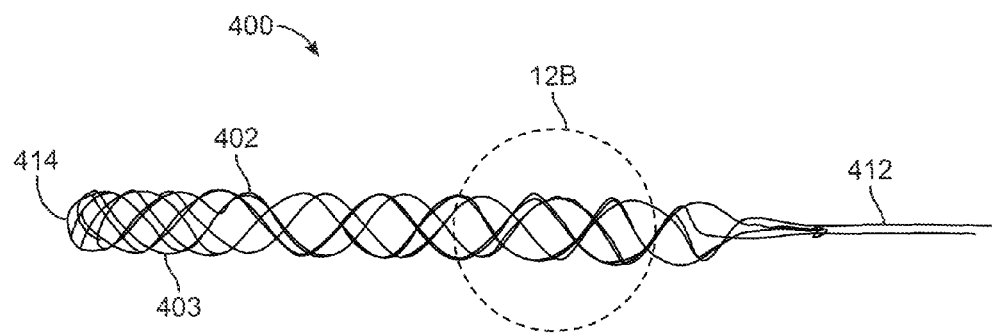
FIGS. 12A to 12F illustrate various stent designs for increasing the ability of a stent to adhere to an occlusion within a vessel.

The retrieval devices described herein can optionally comprise elongated stents 400 as shown in FIGS. 12A to 12E. These stents 400 can include any number of features to better assist the stent 400 in becoming enmeshed into the obstruction. For example, FIG. 12A illustrates a variation of a stent 400 affixed to a shaft 412. As noted herein, the shaft 412 can include a lumen extending therethrough. Alternatively, the shaft 412 can include a solid member with the stent 400 affixed to a distal end thereof. The variation shown in FIG. 12A includes a stent where a distal end 414 that is "closed off" by intersecting elements or wires 402 403. Accordingly, any of the variations of the stents disclosed herein can include an open lumen type stent or a closed lumen type stent as shown in FIG. 12A. As noted herein, the wires forming the stent 400 can comprise a single wire that is wound from a first direction (e.g., from proximal to distal) and then wound back in a second direction (e.g., from distal to proximal).

Figure 12B:
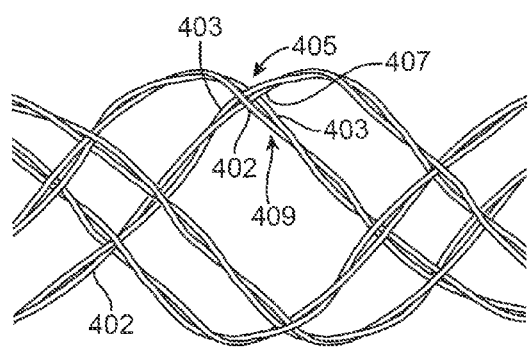

FIG. 12A also illustrates a stent 400 comprised of twisted wires 402 or elements. For example, FIG. 12B shows a magnified view of the section 12B in FIG. 12A. As illustrated, the elements 402 403 are twisted to increase the surface area at the exterior perimeter of the stent 400. The twisting or spiraling of the elements 402 403 creates additional surface area to increase the ability of the stent 400 to capture debris, thrombus, foreign body, etc. as the stent is expanded against the debris. The twisting elements 402 403 can twist along the entire length of the stent 400 or along one or more portions of the stent. In certain variations, the twisting of the elements 402 403 is sufficiently loose such that as the stent expands into a clot or obstruction, the twisted pairs slightly separate to allow material to become trapped between the elements making up the pairs. The construction shown in FIGS. 12A and 12B also provide an additional benefit to a retrieval stent. In the illustrated variation, the twisted or spiraling elements interlock with crossing elements to form intersections 405 that provided added radial expansive force. As shown, a first twisted element 407 passes in between elements 402 403 of an intersecting element 409. When in an expanded state, the element on the interior of the intersection 405 (in this case element 403) provides an added outward radial force against the intersection 405. However, since the elements are not affixed but instead are slidable at the intersection 405, the force required to linearlize and compress the stent 400 is reduced due to the fact that the intersections are not affixed but slidable over the adjacent elements. This reduced linearization force allows the stent to be compressed to a small diameter for positioning within a microcatheter but allow for a significant radial expansive force once removed from the microcatheter. This design allows for a reduction in radial force of the stent against the vessel wall when the stent is pulled and removed from the vessel. However, this design also provides a high degree of radial force due to the interweaving of elements when the stent is deployed in the vessel prior to withdrawal of the stent.

Figure 12C:
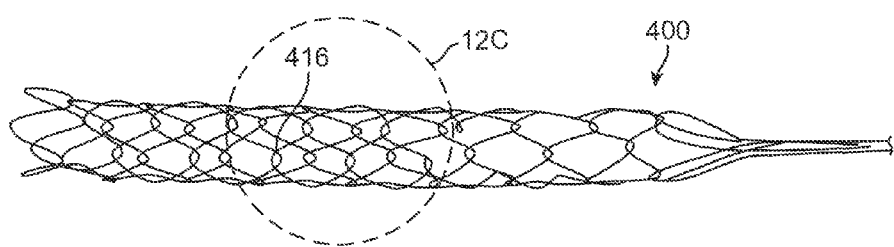
Figure 12D:
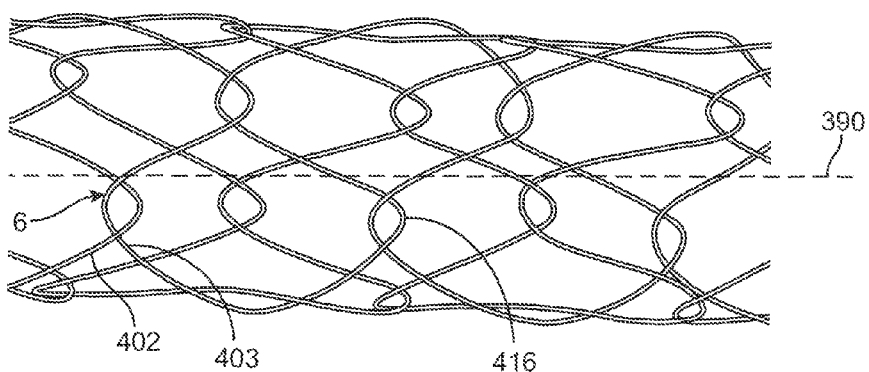
Figure 12E:
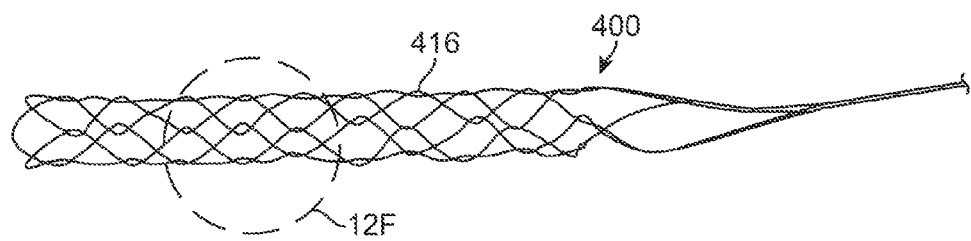
Figure 12F:
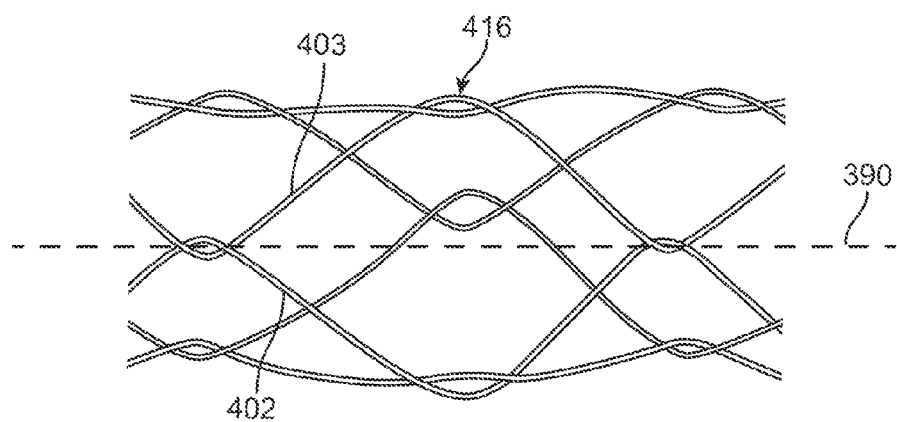

FIGS. 12C to 12F illustrate another variation of types of stents 400 that have an irregular surface at an exterior of the stent 400 that is formed by an intersection of elements 402 403. The intersection or crossing of the elements forms a type of barb or knuckle 416 that creates an irregular surface on the exterior of the stent 400. FIG. 12C illustrates a variation of a stent 400 having a plurality of knuckles 52 that are radially spaced about an axis 390 of the stent 400. FIG. 12E shows another variation of a stent 400 with knuckles 416 aligned with an axis 390 of the stent 400 as shown in FIG. 12D. Although the figures show the axial and radial aligned knuckles 416 on separate devices, both types of knuckles 416 can be incorporated into a single stent structure. Varying the alignment of knuckles can permit increased radial force as the stent expands into the obstruction or increased flexibility as the stent navigates through tortuous anatomy.

Figure 12G:
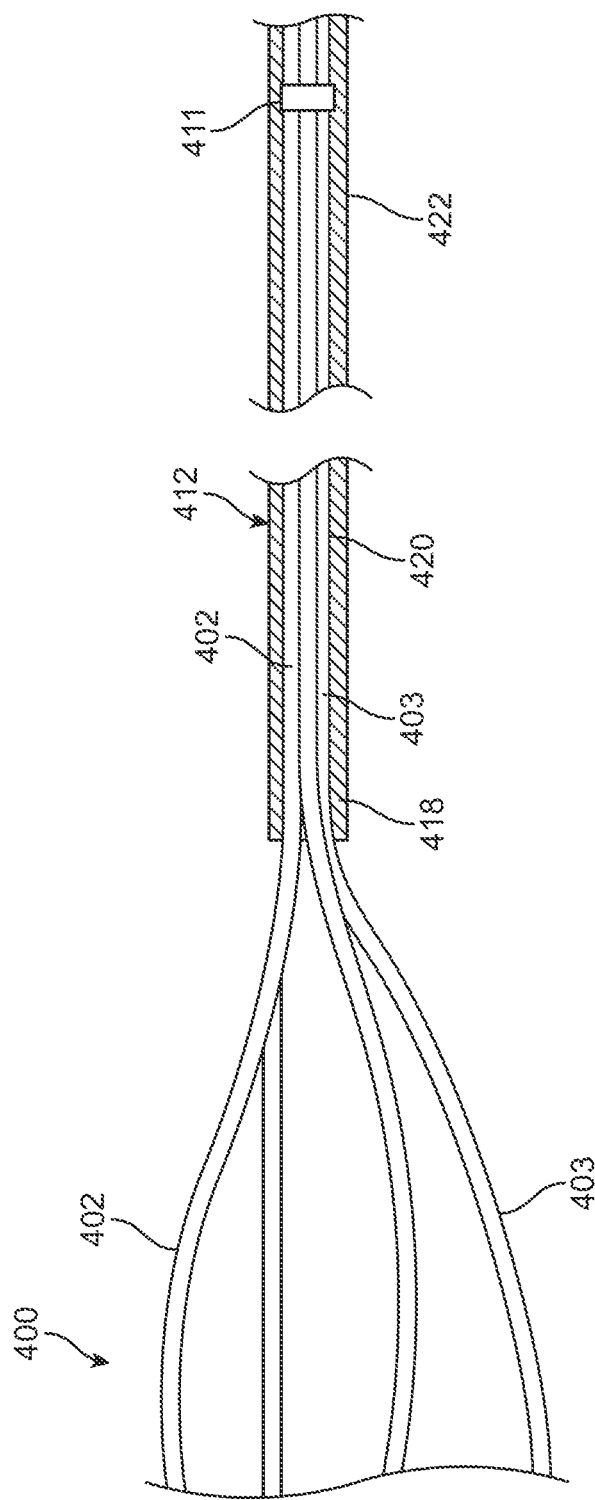
FIG. 12G illustrates a proximal end of the stent structure.

FIG. 12G illustrates a proximal end of the stent structure 400 as shown, a plurality of elements 402 and 403 extend along the shaft 412 and diverge to form the fluid permeable closed proximal end of the stent structure 400. The elements 402 and 403 that extend along the shaft 412 can be covered by a sheath, tube, spiral cut tube, or any structure 418 that prevents separation of the elements 402 403. A variation of the stent structure 402 includes a construction where the elements 402 403 are not glued, welded, or have any similar type of joint in the distal portion 420 of the shaft 412. Instead, the joint 411 is located proximal to the distal section of the shaft 412 in an intermediate section 422. Because joints or other similar features reduce flexibility of the joined structure, positioning the joints 411 in a proximal area allows the distal portion 420 of the shaft to remain flexible.

The methods described herein may also include treating the obstruction prior to attempting to remove the obstruction. Such a treatment can include applying a chemical or pharmaceutical agent with the goal of making the occlusion shrink or to make it more rigid for easier removal. Such agents include, but are not limited to chemotherapy drugs, or solutions, a mild formalin, or aldehyde solution.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

We claim:

1. A medical device for retrieving a clot from within a vessel lumen, the device comprising:
   a delivery wire sized for advancement through a blood vessel, the delivery wire having a distal region and a proximal region;
   a stent coupled to the distal region of the delivery wire;
   an inverting funnel having a first end portion coupled to the distal region of the delivery wire and a free second end portion, the funnel having (a) a first position in which the first end portion is distal of the second end portion, and (b) a second position in which the second end portion is distal of the first end portion such that the funnel surrounds at least a portion of the stent,
   wherein, when the device is positioned within the vessel lumen such that the stent and the funnel are in an expanded state and the funnel is in the first position, proximal movement of the delivery wire causes the funnel to move from the first position towards the second position.

2. The medical device of claim 1, wherein the funnel is self-expanding.

3. The medical device of claim 1, wherein the funnel is a braid.

4. The medical device of claim 3, wherein the braid is formed of a plurality of wires that are drawn filled tubes.

5. The medical device of claim 3, wherein the braid is formed of a plurality of wires that are drawn filled tubes having a platinum core.

6. The medical device of claim 3, wherein the braid is formed of 48-96 wires.

7. The medical device of claim 3, wherein the braid is formed of wires having a diameter of about 0.001 inches to about 0.002 inches.

8. The medical device of claim 1, wherein the funnel has a single layer.

9. The medical device of claim 1, wherein the funnel has multiple layers.

10. The medical device of claim 1, wherein the funnel is attached directly to the stent.

11. The medical device of claim 1, wherein the first end portion of the funnel is fixed relative to a proximal terminus of the stent.

12. The medical device of claim 1, wherein the funnel and the stent are fixed to the delivery wire at a common junction.

13. The medical device of claim 1, wherein the first end portion of the funnel is coupled to the delivery wire proximal of the stent.

14. The medical device of claim 1, wherein the first end portion of the funnel is fixed to the delivery wire at a location proximal of and spaced apart from the stent.

15. The medical device of claim 1, wherein a portion of the funnel has a pre-set shape.

16. The medical device of claim 1, wherein the funnel is slidable relative to the delivery wire.

17. The medical device of claim 1, wherein the funnel is slidable relative to the delivery wire and the stent.

18. The medical device of claim 1 wherein, the funnel includes a funnel wall extending between the first end portion and the second end portion, and wherein a portion of the funnel wall extends distally beyond the first end portion when the funnel is expanded into the first position prior to proximal movement of the delivery wire.

19. The medical device of claim 1, wherein the stent comprises a stentriever.

20. The medical device of claim 1, wherein the delivery wire is sized for advancement through a microcatheter.

21. The medical device of claim 1, wherein the funnel is configured to invert in conveyor belt fashion to cover the stent.

22. The medical device of claim 1, wherein the funnel is configured to be held in place during inversion by frictional force against the blood vessel wall.

23. A medical device for retrieving a clot from within a vessel lumen, the device comprising:
   a delivery wire sized for advancement through a blood vessel, the delivery wire having a distal region and a proximal region;
   a stent having a proximal portion fixed to the distal region of the delivery wire and a distal portion;
   a braid having a fixed end and an opposing free open end, the fixed end fixed to the delivery wire at or proximal to the proximal portion of the stent,
   wherein, when the device is positioned within the vessel lumen such that the stent and the braid are in an expanded state and the open end of the braid is proximal of the fixed end, proximal movement of the delivery wire causes the stent to move proximally while the braid engages the vessel wall such that friction of the braid against the vessel wall causes the open end of the braid to invert over at least a portion of the stent so that the open end of the braid is distal to the fixed end, thereby covering at least a portion of the stent.

24. The medical device of claim 23, wherein the braid is self-expanding.

25. The medical device of claim 23, wherein the braid is formed of a plurality of wires that are drawn filled tubes.

26. The medical device of claim 23, wherein the braid is formed of a plurality of wires that are drawn filled tubes having a platinum core.

27. The medical device of claim 23, wherein the braid is formed of 48-96 wires.

28. The medical device of claim 23, wherein the braid is formed of wires having a diameter of about 0.001 inches to about 0.002 inches.

29. The medical device of claim 23, wherein the braid has a single layer.

30. The medical device of claim 23, wherein the braid has multiple layers.

31. The medical device of claim 23, wherein the braid is attached directly to the stent.

32. The medical device of claim 23, wherein the fixed end of the braid is fixed relative to a proximal terminus of the stent.

33. The medical device of claim 23, wherein the braid and the stent are fixed to the delivery wire at a common junction.

34. The medical device of claim 23, wherein the fixed end of the braid is coupled to the delivery wire proximal of the stent.

35. The medical device of claim 23, wherein the fixed end of the braid is fixed to the delivery wire at a location proximal of and spaced apart from the stent.

36. The medical device of claim 23, wherein a portion of the braid has a pre-set shape.

37. The medical device of claim 23, wherein the braid is slidable relative to the delivery wire.

38. The medical device of claim 23, wherein the braid is slidable relative to the delivery wire and the stent.

39. The medical device of claim 23, wherein the braid includes a braid wall extending between the fixed end and the open end, and wherein a portion of the braid wall extends distally beyond the fixed end when the braid is expanded into the first position prior to proximal movement of the delivery wire.

40. The medical device of claim 23, wherein the stent comprises a stentriever.

41. The medical device of claim 23, wherein the delivery wire is sized for advancement through a microcatheter.

42. The medical device of claim 23, wherein the braid is configured to invert in conveyor belt fashion to cover the stent.

43. The medical device of claim 23, wherein the braid is configured to be held in place during inversion by frictional force against the blood vessel wall.

44. The medical device of claim 23, wherein the fixed end of the braid is closed.

45. A method for retrieving a clot from within a vessel lumen of a patient using a retrieval device, the method comprising:
positioning the retrieval device within the vessel lumen at or near the clot, wherein the retrieval device is coupled to a distal portion of a delivery wire, the retrieval device including (i) a stent coupled to the delivery wire and (ii) a funnel having a first end portion coupled to the delivery wire and a free second end portion;
expanding the retrieval device within the lumen into a first configuration such that at least a portion of the funnel expands into contact with the vessel wall and the coupled first end portion of the funnel is distal of the free second end portion of the funnel;
securing at least a portion of the clot via the stent,
pulling the delivery wire proximally, thereby transforming the retrieval device into a second configuration in which the second end portion of the funnel is distal of the first end portion such that the funnel surrounds at least a portion of the stent; and
withdrawing the retrieval device and the at least a portion of the clot from the patient.

46. The method of claim 45, wherein pulling the stent proximally suffices to invert the funnel and thereby cover the stent.

47. The method of claim 45, wherein the funnel is self-expanding.

48. The method of claim 45, wherein the funnel is a braid.

49. The method of claim 45, wherein the funnel has a single layer.

50. The method of claim 45, wherein the funnel has multiple layers.

51. The method of claim 45, wherein the funnel is attached directly to the stent.

52. The method of claim 45, wherein the first end portion of the funnel is fixed relative to a proximal terminus of the stent.

53. The method of claim 45, wherein the funnel and the stent are fixed to the delivery wire at a common junction.

54. The method of claim 45, wherein the first end portion of the funnel is coupled to the delivery wire proximal of the stent.

55. The method of claim 45, wherein the first end portion of the funnel is fixed to the delivery wire at a location proximal of and spaced apart from the stent.

56. The method of claim 45, wherein a portion of the funnel has a pre-set shape.

57. The method of claim 45, further comprising sliding the funnel along the delivery wire.

58. The method of claim 45, further comprising sliding the funnel along the delivery wire relative to the stent.

59. The method of claim 45, wherein the funnel includes a funnel wall extending between the first end portion and the second end portion, and wherein a portion of the funnel wall extends distally beyond the first end portion when retrieval device is in the first configuration prior to proximal movement of the delivery wire.

60. The method of claim 45, wherein the stent comprises a stentriever.

61. The method of claim 45, further comprising advancing the delivery and retrieval device through a microcatheter.

62. The method of claim 45, wherein pulling the delivery wire proximally includes inverting the funnel.

63. The method of claim 62, wherein the funnel is configured to be held in place during inversion by frictional force against the blood vessel wall.

64. The method of claim 45, wherein the first end portion of the funnel is closed.

* * * * *